US008676332B2

(12) United States Patent
Fahey

(10) Patent No.: US 8,676,332 B2
(45) Date of Patent: Mar. 18, 2014

(54) SYSTEMS AND METHODS OF POWERED MUSCLE STIMULATION USING AN ENERGY GUIDANCE FIELD

(75) Inventor: Brian J. Fahey, Palo Alto, CA (US)

(73) Assignee: Niveus Medical, Inc., Palo Alto, CA (US)

( * ) Notice: Subject to any disclaimer, the term of this patent is extended or adjusted under 35 U.S.C. 154(b) by 0 days.

(21) Appl. No.: 13/568,859

(22) Filed: Aug. 7, 2012

(65) Prior Publication Data

US 2012/0303076 A1    Nov. 29, 2012

Related U.S. Application Data

(62) Division of application No. 12/710,243, filed on Feb. 22, 2010, now Pat. No. 8,433,403.

(60) Provisional application No. 61/208,119, filed on Feb. 20, 2009, provisional application No. 61/230,587, filed on Jul. 31, 2009.

(51) Int. Cl.
*A61N 1/00* (2006.01)

(52) U.S. Cl.
USPC .......................................................... 607/48

(58) Field of Classification Search
USPC .......................................................... 607/48
See application file for complete search history.

(56) References Cited

U.S. PATENT DOCUMENTS

| 4,108,146 A * | 8/1978 | Golden ................ 607/104 |
| 4,390,023 A | 6/1983 | Rise |
| 4,480,830 A | 11/1984 | Petrofsky et al. |
| 4,580,569 A | 4/1986 | Petrofsky |
| 4,619,266 A | 10/1986 | Hodgson |
| 4,736,752 A | 4/1988 | Munck et al. |
| 4,805,636 A | 2/1989 | Barry et al. |
| 4,811,742 A | 3/1989 | Hassel et al. |
| 4,838,272 A | 6/1989 | Lieber |
| 4,867,166 A | 9/1989 | Axelgaard et al. |
| 4,962,761 A * | 10/1990 | Golden ................ 607/104 |
| 4,969,468 A | 11/1990 | Byers et al. |
| 5,010,896 A | 4/1991 | Westbrook |
| 5,016,635 A | 5/1991 | Graupe |
| 5,070,873 A | 12/1991 | Graupe et al. |
| 5,097,828 A * | 3/1992 | Deutsch ................ 607/104 |
| 5,314,423 A | 5/1994 | Seney |

(Continued)

FOREIGN PATENT DOCUMENTS

| FR | 2596654 A | 10/1987 |
| JP | 2001-025510 | 1/2001 |

(Continued)

OTHER PUBLICATIONS

Baker et al.; Effects of waveform on comfort during neuromuscular electrical stimulation; Clin Ortho Res; vol. 233; pp. 75-85; Aug. 1988.

(Continued)

*Primary Examiner* — Christopher D Koharski
*Assistant Examiner* — Philip Edwards
(74) *Attorney, Agent, or Firm* — Shay Glenn LLP

(57) ABSTRACT

NMES systems and methods for stimulating muscle tissue, and in some embodiments deep muscle tissue. The impedance near the surface of the skin is controllably increased to increase the percentage of energy delivered to a subject that stimulates muscle tissue.

49 Claims, 15 Drawing Sheets

(56) References Cited

U.S. PATENT DOCUMENTS

| | | | |
|---|---|---|---|
| 5,336,255 A * | 8/1994 | Kanare et al. | 607/149 |
| 5,397,338 A | 3/1995 | Grey et al. | |
| 5,507,788 A | 4/1996 | Lieber | |
| 5,549,656 A | 8/1996 | Reiss | |
| 5,674,262 A | 10/1997 | Tumey | |
| 5,702,323 A | 12/1997 | Poulton | |
| 5,702,429 A | 12/1997 | King | |
| 5,843,152 A | 12/1998 | Tu et al. | |
| 5,871,526 A * | 2/1999 | Gibbs et al. | 607/104 |
| 5,902,328 A | 5/1999 | LaFontaine et al. | |
| 6,216,704 B1 | 4/2001 | Ingle et al. | |
| 6,266,558 B1 | 7/2001 | Gozani et al. | |
| 6,301,500 B1 | 10/2001 | Van Herk et al. | |
| 6,324,432 B1 | 11/2001 | Rigaux et al. | |
| 6,341,237 B1 | 1/2002 | Hurtado | |
| 6,350,276 B1 * | 2/2002 | Knowlton | 607/104 |
| 6,480,731 B1 | 11/2002 | DeLuca et al. | |
| 6,505,078 B1 | 1/2003 | King et al. | |
| 6,567,696 B2 | 5/2003 | Voznesensky et al. | |
| 6,829,510 B2 | 12/2004 | Nathan et al. | |
| 6,840,955 B2 | 1/2005 | Ein | |
| 6,944,503 B2 | 9/2005 | Crowe et al. | |
| 7,146,220 B2 | 12/2006 | Dar et al. | |
| 7,172,564 B2 | 2/2007 | Bosco | |
| 7,204,832 B2 | 4/2007 | Altshuler et al. | |
| 7,221,980 B2 | 5/2007 | Kotlik et al. | |
| 7,236,832 B2 | 6/2007 | Hemmerling et al. | |
| 7,257,448 B2 | 8/2007 | Crowe et al. | |
| 7,276,058 B2 | 10/2007 | Altshuler et al. | |
| 7,473,251 B2 | 1/2009 | Knowlton et al. | |
| 7,483,738 B2 | 1/2009 | Tamarkin et al. | |
| 7,499,746 B2 | 3/2009 | Buhlmann et al. | |
| 8,216,218 B2 | 7/2012 | Burns et al. | |
| 8,265,763 B2 | 9/2012 | Fahey | |
| 8,285,381 B2 | 10/2012 | Fahey | |
| 2002/0049483 A1 * | 4/2002 | Knowlton | 607/101 |
| 2002/0143365 A1 | 10/2002 | Herbst | |
| 2002/0151951 A1 | 10/2002 | Axelgaard et al. | |
| 2003/0229385 A1 * | 12/2003 | Elkins | 607/104 |
| 2004/0044384 A1 | 3/2004 | Leber et al. | |
| 2004/0173220 A1 | 9/2004 | Harry et al. | |
| 2004/0254624 A1 | 12/2004 | Johnson | |
| 2005/0288730 A1 | 12/2005 | Deem et al. | |
| 2006/0142816 A1 * | 6/2006 | Fruitman et al. | 607/48 |
| 2007/0106343 A1 | 5/2007 | Monogue et al. | |
| 2007/0203435 A1 | 8/2007 | Novak | |
| 2008/0161883 A1 | 7/2008 | Conor | |
| 2008/0195010 A1 | 8/2008 | Lai et al. | |
| 2009/0012436 A1 | 1/2009 | Lanferman et al. | |
| 2010/0217349 A1 | 8/2010 | Fahey | |
| 2011/0082517 A1 | 4/2011 | Brezel et al. | |
| 2011/0112605 A1 | 5/2011 | Fahey | |
| 2013/0030277 A1 | 1/2013 | Fahey | |

FOREIGN PATENT DOCUMENTS

| | | |
|---|---|---|
| JP | 2002-052000 | 2/2002 |
| KR | 10-866543 B | 11/2008 |
| WO | WO 01/52759 A1 | 7/2001 |
| WO | WO 03/086217 A1 | 10/2003 |
| WO | WO 2004/089185 A2 | 10/2004 |
| WO | WO 2004/098703 A2 | 11/2004 |
| WO | WO 2005/075018 A1 | 8/2005 |
| WO | WO 2005/105203 A1 | 11/2005 |
| WO | WO 2007/017778 A2 | 2/2007 |
| WO | WO 2007/041540 A1 | 4/2007 |
| WO | WO 2007/046886 A1 | 4/2007 |
| WO | WO 2008/032282 A2 | 3/2008 |
| WO | WO 2008/034607 A1 | 3/2008 |
| WO | WO 2008/075250 A1 | 6/2008 |
| WO | WO 2008/116232 A1 | 9/2008 |
| WO | WO 2009/009661 A1 | 1/2009 |

OTHER PUBLICATIONS

Bennie et al.; Toward the optimal waveform for electrical stimulation of human muscle; Eur J Appl Physiol; vol. 88; pp. 13-19; Nov. 2002.

Lacey et al.; Reductions in the amount of time spent in direct patient care by staff nurses in North Carolina; North Carolina Center for Nursing; Aug. 2002.

Lyons et al.; An investigation of the effect of electrode size and electrode location on comfort during stimulation of the gastrocnemius muscle; Medical Engineering & Physics; vol. 26; pp. 873-878; Dec. 2004.

Miklavcic et al.; Electrical Properties of Tissues; Wiley Encyclopedia of Biomedical Engineering; (year of publication is sufficiently earlier than the effective U.S. filing date and any foreign priority date) 2006.

Morris, Peter E.; Moving our critically ill patients: mobility barriers and benefits; Critical Care Clinics; vol. 23; pp. 1-20; Jan. 2007.

Petrofsky et al.; Estimation of the distribution of intramuscular current during electrical stimulation of the quadriceps muscle; Eur J Appl Physiol; vol. 103(3); pp. 265-273; Jun. 2008.

Prausnitz, Mark R.; The effects of electrical current applied to skin: a review for transdermal drug delivery; Advanced Drug Delivery Reviews; vol. 18; pp. 395-425; Feb. 8, 1996.

Rafolt et al.; Dynamic force responses in electrically stimulated triceps surae muscles: effects of fatigue and temperature; Artificial Organs; vol. 23; No. 5; pp. 436-439; May 1999.

Solomon et al.; The effects of TENS, heat, and cold on the pain thresholds induced by mechanical pressure in healthy volunteers; Neuromodulation; vol. 6; No. 2; pp. 102-107; Apr. 2003.

Stecker et al.; Mechanisms of electrode induced injury. Part 1: theory; Am. J. End Tech.; vol. 46; pp. 315-342; Dec. 2006.

Suganuma et al.; Measurement of tension of tendon tissue based on electrical impedance; J. Ortho Science; vol. 9; pp. 302-309; (year of publication is sufficiently earlier than the effective U.S. filing date and any foreign priority date) 2004.

Zanotti et al.; Peripheral muscle strength training in bed-bound patients with COPD receiving mechanical ventilation: effect of electrical stimulation; Chest; vol. 124; No. 1; pp. 292-296; Jul. 2003.

Covidien; Principles of Electrosurgery (white paper); p. 3; accessed from http://www.asit.org/assets/documents/Prinicpals_in_electrosurgery.pdf on Dec. 12, 2012, 4 pages.

Xodus Medical; Electrosurgery Frequency Spectrum; accessed from http://www.xodusmedical.com/Modules/Product/ProductTraining.aspx?Launch=Electrosurgical on Dec. 12, 2012; 1 page.

Snyder-Mackler et al.; Use of electrical stimulation to enhance recovery of quadriceps femoris muscle force production in patients following anterior cruciate ligament reconstruction; Phys Ther.; 74(10):901-7; Oct. 1994.

Fahey et al; U.S. Appl. No. 13/926,827 entitled "Devices and Systems for Stimulation of Tissues" filed Jun. 25, 2013.

* cited by examiner

SYSTEMS AND METHODS OF POWERED MUSCLE STIMULATION USING AN ENERGY GUIDANCE FIELD

CROSS-REFERENCE TO RELATED APPLICATIONS

This application is a divisional application of pending U.S. application Ser. No. 12/710,243, filed Feb. 22, 2010, which application claims the benefit of the following U.S. Provisional Applications: Application No. 61/208,119, filed Feb. 20, 2009; and Application No. 61/230,587, filed Jul. 31, 2009, which are incorporated by reference herein.

This application is related to the following patent applications: Application No. 61/260,324, filed Nov. 11, 2009; application Ser. No. 12/497,230, filed Jul. 2, 2009; Application No. 61/189,558, filed Aug. 19, 2008; application Ser. No. 12/548,155, filed Aug. 26, 2009, Application No. 61/190,602, filed Aug. 29, 2008; and Application No. 61/201,877, filed Dec. 15, 2008, all of which are incorporated herein by reference.

BACKGROUND OF THE INVENTION

Neuromuscular electrical stimulation ("NMES"), which is also referred to as powered muscle stimulation, functional muscle stimulation, electrical muscle stimulation, is a known technology with many therapeutic uses, including pain relief, prevention or retardation of disuse atrophy, and improvement of local blood circulation. NMES is typically delivered as an intermittent and repeating series of short electrical pulses delivered transcutaneously by surface electrodes that are attached to a person's skin. The electrical pulses are delivered to muscle tissue and/or a muscle nerve to induce muscle contraction. The electrodes may be secured to the skin using straps, adhesives, or other mechanisms, and often contain a coupling layer composed of hydrogel that is capable of enhancing the efficiency of energy transfer from the electrode to the skin and underlying tissues.

Individuals who may benefit greatly from NMES therapy are those who are immobilized or confined to bed rest. Immobilization leads to muscle atrophy and weakness, and has severe effects on a person's physical capacity. Following immobilization, a previously active and functional person will typically require extensive physical therapy to reclaim their prior level of functionality. NMES may help prevent or retard muscle atrophy during immobilization by stimulating the muscle.

Critically ill patients comprise a subgroup of immobilized individuals. While virtually all of these patients are confined to bed rest, many are also suffering from conditions such as coma or are receiving interventions (such as mechanical ventilation) that generally require sedation and/or analgesia. Sedated or comatose patients are at a great risk for muscle atrophy because even simple voluntary movements (such as shifting arms/legs in bed or moving one's feet) are often not performed. Consequently, critically ill patients face long paths to recovery that are generally measured in months as opposed to days or weeks.

As part of the care for their acute illness, many critically ill patients receive I/V fluids, antibiotics, and other interventions. One common side effect of these medical treatments in immobilized patients is the development of tissue edema. Generally speaking, tissue edema occurs as bodily fluids accumulate in 'the third space', or the region outside of both cells and vessels. Edema is often caused by microvasculature leakage, and typically results in tissue swelling. The presence of edema will generally negatively affect the performance of NMES, in many cases limiting the ability of the technology to adequately induce muscle contraction. This is particularly true when attempting to stimulate deep-lying muscles, such as the quadriceps, hamstrings, gluteals, rectus abdominus, transversus abdominus, internal and external obliques, pelvic floor, multifidus, erector spinae, longissimus thoracis, diaphragm, using non-invasive electrodes placed upon the surface of the skin.

There are several mechanisms of action by which tissue edema may affect NMES therapy. Tissue swelling may increase the distance between the surface of the skin and underlying muscle, resulting in a lower current density that reaches deep target muscles. Additionally, excessive ionic fluid in tissues may decrease the electrical impedance of tissue, particularly in superficial regions. The decrease in impedance in superficial regions can act to 'short-circuit' skin electrodes. The lower impedance path in superficial tissue regions can also act as a mechanism to reduce the current density in deeper muscle tissues. The latter of these mechanisms may be the dominant factor associated with decreased NMES performance in edematous patients. Although previous work in the medical literature has noted that certain types of electrical stimulation may prevent the onset of local edema after traumatic injury, these therapies have not been shown to prevent or reduce widespread edema in cases involving non-traumatic or multi-factorial medical conditions.

In many edematous patients, it is not possible to reliably stimulate the contraction of deep muscles using surface electrodes and energy levels that fall within regulatory and governing body standards (e.g., the US FDA, ANSI, and IEC). Although the use of higher energy levels may increase NMES efficacy, increasing the amplitude of delivered energy (and thus the current density in tissue), increases the risk of burns, nerve and/or muscle damage, and other potential complications, as detailed by Prausnitz *Advanced Drug Delivery Reviews* 18:395-425, 2006 and Stecker et al *Am J END Tech.*, 43:315-342, 2006, both of which are incorporated herein by reference. This is particularly true for the 'short circuit' condition because large current densities will be present in superficial tissues and smaller current densities will be present in the muscle tissue. These and other factors limit the application of NMES therapy to edematous patients and to immobilized critically ill patients as a whole, a group that has been hypothesized to potentially benefit significantly from the therapy (Morris et al., *Critical Care Clinics*, 23:1-20, 2007, which is incorporated herein by reference).

Short-duration, localized application of low temperature thermal energy to the skin will reduce the temperature of superficial tissues and can induce a number of potentially medically-useful effects. For example, surface cooling can create a "reverse" temperature gradient between superficial tissue and deep-lying tissue, with deep-lying tissue remaining relatively warmer (i.e., closer to normal body temperature) than superficial tissue.

One application of reverse thermal gradients that has been described involves the combination of surface cooling with the targeted transcutaneous delivery of high energy radiofrequency (RF), optical, photo-acoustic, acoustic, infrared, electromagnetic, or other types of stimuli to tissues below the skin surface. Generally, these applications seek to significantly raise the temperature of tissues below the skin surface for the purposes of ablation, tissue (e.g., collagen) remodeling, or other dermatologic or therapeutic reasons. These applications seek to apply energy to target tissues non-invasively without raising temperatures in the skin and other superficial tissues to avoid damaging tissue not intended for treatment. The reverse thermal gradient assists this procedure by cooling superficial tissue without significantly cooling the deeper tissue that is intended to be treated by an increase in temperature. Accordingly, temperatures in superficial regions are kept below levels that would cause damage, even though a portion of the energy stimulus is absorbed in these regions.

A subset of thermal gradient applications described above use high amplitude RF or other forms of electromagnetic/electric energy to significantly raise temperatures in target tissue regions (e.g., hair follicles, collagen, etc.). To be effective, these treatments require temperatures in target regions of tissue to exceed about 43° C., with most applications requiring elevating tissue temperatures to about 60° C. or higher. Near these temperatures, moisture in cells and extracellular fluid is evaporated, resulting in increased tissue impedance with increased temperature. Reverse thermal gradients and surface cooling of tissues can assist energy delivery by forcing superficial tissue temperatures to remain only minimally elevated over normal body temperature, thus lowering the superficial tissue impedance (relative to the overheated tissues below), allowing for more energy to be delivered through the superficial tissue to the deeper target regions below.

For ablative, cosmetic, and other therapeutic procedures, muscle contraction is generally not induced by energy that is delivered to tissue. In virtually all cases, this is preferable, as muscle contraction in the region of desired treatment would complicate the intervention. For example, RF energy utilized by many devices is intentionally delivered in a frequency range, for example, about 100 to about 500 kHz, which is too high to elicit muscle contraction.

Additionally, in cosmetic, ablative, and therapeutic applications that use surface cooling to prevent skin burns, the reverse thermal gradient is applied at the anatomical location where energy transmits across the skin, or in larger regions that include the location at which energy is transmitted across the skin. These systems and methods utilizing the reverse thermal gradient are optimized for the energy amplitudes, frequency ranges, and temperature ranges that are common in these ablative, cosmetic, and therapeutic procedures. For muscle stimulators operating at relatively lower energy frequencies and amplitudes, with peak tissue temperatures near normal body temperature, there are drawbacks to lowering skin temperatures in the region where energy transmits across the skin. Doing so will significantly lower the efficiency of energy transfer into the body, markedly decrease the life span of surface stimulation electrodes, and decrease the overall effectiveness of the therapy.

Most muscle stimulators used in modern clinical settings are constant current (or voltage) stimulators, meaning that when tissue impedance increases, the stimulator device will increase the voltage (or current) amplitude of delivered energy (up to a predetermined limit) in an attempt to keep the electrical current (or voltage) delivered to a person constant. Without wishing to be bound by any theory, it is believed that this increase in voltage (or current) will increase energy loss and heat generation in skin electrodes. Although the risk of skin burns (generally a serious concern) may be partially reduced if the skin surface is pre-cooled, increased temperature of skin electrodes will degrade the performance of the electrodes. The most common modern-day skin electrodes used with NMES include a hydrogel coupling layer that serves as both an adhesive and a conductive (coupling) medium. These hydrogels may be composed of more than 50% water, and elevated temperatures will cause electrodes to dry prematurely, dramatically reducing reusability. This factor is particularly important in the ICU setting, where it is desirable to leave one set of electrodes in place for extended periods of time, as repeated placement and removal may cause skin trauma. Additionally, drying of hydrogel layers is a positive feedback phenomenon: as the conductive layer dries, skin/electrode impedance will increase further, causing even more heat generation at the skin, and potentially leading to the dangerous scenario of poor electrode contact due to reduced adhesive properties. This latter scenario is of serious concern, as electrodes with poor contact can cause skin burns very quickly, even when NMES is used in conjunction with surface cooling. Thus, devices employing surface cooling and temperature gradients used in the location of skin electrodes are accompanied by serious limitations if used in conjunction with NMES, since this technique raises tissue impedance in the skin electrode location. Specifically, surface cooling and temperature gradients in the location of the skin electrode(s) will typically not improve energy transfer efficiency to muscles, and may thus increase tissue impedance and decrease electrode performance in a manner that has little or no benefit for NMES.

Transcutaneous electrical nerve stimulators ("TENS") is another type of therapy that has used skin surface cooling combined with transcutaneous energy delivery. Specifically, this therapy has sought to harness the pain relief effects of hot and cold temperatures applied to the skin, and combine them with pain relief effects of nerve stimulation. Although TENS units are typically not operated at sufficient amplitude to cause muscle contraction, muscle stimulation with TENS units is theoretically possible. TENS therapy also applies temperature gradients in the anatomical locations where energy is transmitted through the skin, or over large spans of anatomical areas that include the locations where energy is transmitted through the skin. As described herein, doing so with electrical muscle stimulation therapies significantly lowers the efficiency of energy transfer into the body, markedly decreases the life span of surface stimulation electrodes, and decreases the overall effectiveness of the therapy.

Improved NMES systems and methods of use are needed to overcome deficiencies of current NMES systems and methods of use. For example, improved NMES systems are needed which can perform one or more of the following: more efficiently and effectively transfer stimulating energy to muscle tissue, particularly deep muscle tissue; be used safely and effectively with immobilized and critically ill patients; be used to effectively and safely treat edematous and non-edematous patients. Existing therapies that incorporate surface cooling and/or temperature gradients with transcutaneous energy application do not accomplish the objectives required as they are not optimally configured for use with NMES and are tailored to meet objectives unrelated to improved muscle contraction.

SUMMARY OF THE INVENTION

One aspect of the disclosure is a method of electrically stimulating muscle tissue. The method includes positioning first and second electrodes on a subject in the vicinity of muscle tissue to be stimulated; increasing the electrical impedance of one or more superficial tissues such that the impedance of the one or more superficial tissues is increased relative to the impedance in the muscle tissue to be stimulated; and delivering electrical energy through the muscle tissue from the first electrode to the second electrode, wherein increasing the electrical impedance of the one or more superficial tissues causes a greater percentage of delivered electrical energy to stimulate the muscle tissue to thereby increase muscle contraction.

In some embodiments increasing the electrical impedance of the one or more superficial tissues comprises increasing the electrical impedance of superficial tissues between the first and second electrodes without substantially increasing the electrical impedance of superficial tissues where the first and second electrodes are positioned. In some embodiments the method includes increasing the electrical impedance of one or more superficial tissues that at least partially surround the first and second electrodes. In some embodiments the method includes decreasing the temperature of the one or more superficial tissues in a region between the electrodes to a greater extent than at the locations where the first and second electrodes are positioned. In some embodiments the method includes activating a cooling element positioned between the first and second electrodes.

In some embodiments the positioning step includes positioning the first and second electrodes in the vicinity of a quadricep muscle.

In some embodiments increasing the electrical impedance of the one or more superficial tissues comprises activating a cooling element positioned on the subject between the first and second electrodes. Activating the cooling element can include applying a cold pack to the surface of the skin, pumping a fluid through a cooling element positioned between the first and second electrodes, or activating a thermoelectric device positioned between the first and second electrodes, or any combination thereof. Activating the cooling element can comprise continuously cooling the one or more superficial tissues, or activating the cooling element can comprise intermittently activating the cooling element. Activating the cooling element can create a temperature gradient from the one or more superficial tissues to a depth below the one or more superficial tissues, wherein the temperature of the one or more superficial tissues is the lowest temperature in the gradient. The method can also include deactivating the cooling element before stopping the delivery of electrical energy. Activating the cooling element can include cooling the one or more superficial tissues to a temperature in the range from about 30 to about 40 degrees F.

In some embodiments delivering electrical energy through muscle tissue comprises delivering electrical energy through muscle tissue without increasing the temperature of the muscle tissue above about 40 degrees C.

In some embodiments delivering electrical energy comprises delivering energy using pulses whose spectra contain frequencies of about 10 kHz or lower.

In some embodiments delivering electrical energy comprises delivering energy using pulses with pulse widths from about 100 to about 400 microseconds.

In some embodiments delivering electrical energy comprises delivering energy as a series of pulses delivered with repetition rates from about 30 Hz to about 50 Hz.

In some embodiments delivering electrical energy comprises delivering energy with an alternating series of on and off times.

In some embodiments positioning first and second electrodes on the subject comprises positioning first and second electrodes on an obese or edematous subject.

One aspect of the disclosure is a method of stimulating muscle tissue. The method includes increasing the impedance of one or more superficial tissues in the vicinity of a muscle to be stimulated; and delivering electrical energy to tissue near the muscle to be stimulated with at least two stimulation electrodes, wherein a percentage of the delivered energy stimulates muscle tissue and a percentage of the delivered energy does not stimulate muscle tissue, and wherein increasing the impedance of one or more superficial tissues causes a greater percentage of delivered energy to stimulate muscle tissue than if the impedance of the one or more superficial tissues had not been increased.

In some embodiments increasing the impedance of one or more superficial tissues comprises decreasing the temperature of the one or more superficial tissues in a region between the two surface electrodes.

In some embodiments delivering electrical energy comprises delivering electrical energy to a quadricep muscle.

In some embodiments increasing the impedance of the one or more superficial tissues comprises activating a cooling element positioned between the at least two surface electrodes. Activating the cooling element can comprise maintaining the cooling element at a constant temperature for the duration of a muscle stimulation therapy, decreasing the temperature of the cooling element over the course of a muscle stimulation therapy, intermittently activating the cooling element over the course of a muscle stimulation therapy, and/or deactivating the cooling element after a period of time. Delivering electrical energy can occur after the cooling element has been deactivated.

In some embodiments delivering electrical energy to tissue comprises delivering electrical energy to tissue in an obese or edematous subject.

One aspect of the disclosure is a method of increasing muscle stimulation in a subject. The method includes cooling one or more superficial tissues in the vicinity of muscle tissue to be electrically stimulated such that the temperature of the one or more superficial tissues is lower than the temperature of deep muscle tissue; and applying electrical stimulation to superficial tissue that is not substantially cooled by the cooling step, wherein cooling the one or more superficial tissues increases the amount of muscle contraction relative to an amount of muscle contraction without the cooling step.

In some embodiments cooling the one or more superficial tissues comprises positioning a cooling element on the subject at a location that is different than the region into which electrical energy is applied, wherein the method further comprises activating the cooling element.

In some embodiments applying electrical stimulation comprises applying electrical stimulation between at least two surface electrodes.

In some embodiments applying electrical stimulation comprises increasing the amount of muscle contraction in a quadricep muscle.

In some embodiments cooling one or more superficial tissues in the vicinity of muscle tissue comprises cooling one or more superficial tissues of an obese or edematous subject.

One aspect of the disclosure is a muscle stimulation system. The system includes a stimulation pad comprising a plurality of electrodes, wherein the stimulation pad is adapted to be positioned on the patient such that the electrodes are in position to provide stimulating energy to muscle tissue; a cooling element adapted to be positioned on the patient between the plurality of electrodes and at a location that is different than the location on which the electrodes are positioned, and wherein the cooling element is configured to cool one or more superficial tissues to increase the impedance of the one or more superficial tissues; and a stimulation control unit in communication with the plurality of electrodes and configured to deliver the stimulating energy to the electrodes to stimulate the contraction of muscle tissue.

In some embodiments the cooling element is configured to substantially avoid cooling of superficial tissue where the electrodes are positioned.

In some embodiments the cooling element is adapted to substantially eliminate superficial current paths.

In some embodiments the stimulation pad comprises the cooling element.

In some embodiments the cooling element has a width and the plurality of electrodes span a width, and the width of the cooling element is greater than the width of the plurality of electrodes. The width of the cooling element can be configured to substantially prevent superficial arcing around the cooling element.

In some embodiments the system further comprises a cooling element control unit which is adapted to control the operation of the cooling element. The cooling element control unit can be in fluid communication with the cooling element and can be configured to control the flow of a fluid through the cooling element. The cooling element control unit can include a pump configured to pump the fluid through the cooling element. The cooling element can include an internal lumen in fluid communication with the cooling element control unit. The cooling element control unit can be configured to control a thermoelectric element.

One aspect of the disclosure is a muscle stimulation system. The system includes a plurality of stimulation electrodes adapted to be positioned on a subject; a cooling element in communication with a cooling element control unit, wherein the cooling element control unit is configured to control the cooling element to decrease the temperature of one or more superficial tissues, and wherein the cooling element is configured to be positioned on the subject at a location where the plurality of stimulation electrodes are not positioned; and a stimulation control unit in communication with the plurality of stimulating electrodes.

In some embodiments the cooling element control unit is configured to control the temperature of the cooling element. In some embodiments the cooling element control unit is configured to maintain the cooling element at a substantially constant temperature, while in some embodiments the cooling element control unit is configured to decrease the temperature of the cooling element after it has been activated.

In some embodiments the cooling element control unit is configured to activate the cooling element. The cooling element control unit can be configured to deactivate the cooling element while the stimulation control unit is delivering electrical stimulation to the plurality of electrodes. The cooling element control unit can be configured to intermittently activate the cooling element.

In some embodiments the cooling element is sized and shaped to be disposed between the plurality of stimulation electrodes, and may be sized and shaped to be disposed at least partially surrounding the plurality of electrodes.

In some embodiments the plurality of electrodes are integrated into a simulation pad.

In some embodiments the cooling element is integrated into the stimulation pad.

In some embodiments the cooling element has an internal lumen therein in fluid communication with the cooling element control unit, and wherein the cooling element control unit comprises a pump to pump fluid through the cooling element.

In some embodiments the control element is a thermoelectric device, and wherein the cooling element control unit is adapted to control the thermoelectric device.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A description of the features and advantages of the present disclosure will be obtained by reference to the following detailed description that sets forth illustrative embodiments, in which the principles of the disclosure are utilized, and the accompanying drawings in which.

DETAILED DESCRIPTION OF THE INVENTION

The disclosure provides systems and methods of improving NMES therapy by providing a more efficient transfer of electrical energy to muscle tissue, and in some embodiments to deep-lying muscle tissue. The improved NMES therapies described herein may be used to replace current NMES therapies, can be used to treat edematous as well as non-edematous patients, and may be beneficial for treating critically-ill, immobilized patients. In general, the disclosure relates to electrical muscle stimulation coupled with an energy guidance field that drives electrical energy towards muscle tissue, and in some instances towards deep-lying muscle tissue.

In the applications of NMES herein, electrical energy is applied to muscle tissue transcutaneously by surface electrodes that are secured to a person's skin. The disclosure herein may provide ways to increase the amount of electrical energy that is delivered to the muscle without increasing the amount of electrical energy delivered to the patient. That is, a greater percentage of the electrical energy delivered to the subject is delivered to muscle tissue (as opposed to other tissue), which provides for more efficient muscle stimulation.

A greater percentage of the electrical energy is delivered to muscle tissue by creating an energy guidance field to drive the energy towards muscle tissue.

Figure 1A:
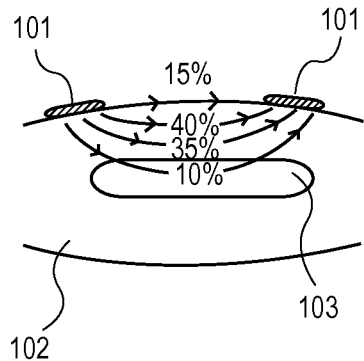
FIG. 1 illustrate how a cooling element can affect electrical current paths through tissue.

FIGS. 1A-1D illustrate side-views of an exemplary embodiment that increase the efficiency of muscle stimulation using NMES. FIG. 1A shows a lateral cross-sectional view of limb 102 of a generally healthy patient with two surface electrodes 101 attached thereto. Electrodes 101 are in communication with a stimulation unit (not shown) which is adapted to deliver current to the electrodes and thereby deliver current through the patient's tissue. FIG. 1A illustrates the direction that the current is traveling (indicated by the arrows) and indicates the percentage of the energy that is reaching a given region of tissue within limb 102. As shown, only a relatively small percentage of the electrical current entering limb 102 reaches deep-lying muscle tissue 103 (shown as 10%).

Figure 1B:
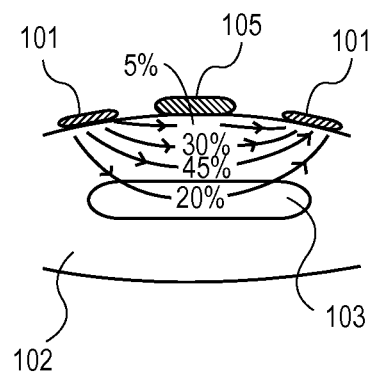

FIG. 1B illustrates limb 102 from FIG. 1A but includes a surface cooling element 105 placed in contact with the surface of the skin, and is disposed on the skin at a location between stimulation electrodes 101. Cooling element 105 generally creates an energy guidance field to drive energy deeper towards muscle tissue. In this embodiment, cooling element 105 creates a temperature gradient from the surface of the skin to a location below the surface of the skin. The surface of the skin can be considered the low temperature end of the temperature gradient. The frequencies of electrical energy utilized by muscle stimulators are generally lower (generally lower than about 10 kHz) than those used in ablative or cosmetic applications (generally greater than about 300 kHz for RF and greater than about 3 GHz for microwave), and thus typically do not generate significant tissue heating, especially in deep tissue regions. Additionally, the use of muscle stimulators typically does not produce tissue temperatures greater than about 40° C. (consistent with many regulatory and governing body guidelines—see Prausnitz 2006 above). For tissue temperatures below 40° C., the effect of temperature on tissue impedance is generally opposite that found at the higher temperatures used during ablative and cosmetic procedures, with tissue impedance increasing by about 2%/° C. (see Miklavcic et al, *Electrical Properties of Tissues*, Wiley Encyclopedia of Biomedical Engineering, 2006, which is incorporated herein by reference). When the tissue nearest the surface of the skin is cooled due to the application of cooling element 105, a three-dimensional temperature gradient will be created in the tissue, which will essentially create a 3-dimensional impedance gradient where the impedance of a tissue will increase in proportion to the degree to which it is cooled. The amount of tissue impedance increase from body temperature impedance level is therefore at least partially dependent on the distance between cooling element 105 and the tissue. Tissues nearest the surface where cooling element 105 is disposed are cooled the most and will experience the largest impedance increases relative to body temperature impedance levels. The impedance at depths near muscle tissue 103 will increase less (if at all) than the impedance of the tissue directly under cooling element 105. NMES coupled with surface cooling therefore has the opposite effect that superficial cooling has when used with higher temperature applications such as ablation or cosmetic procedures described above.

In some embodiments the cooling element lowers the skin temperature in the region of cooling to be in the range from about 30 to about 40° F. Maintaining surface temperatures in this range may create a thermal gradient sufficient to change local tissue impedance and increase the efficiency of energy transfer during NMES. Accordingly, the degree of muscle contraction achievable with a given amount of stimulation energy may be increased. Alternatively, surface temperatures cooler than 30° F. and warmer than 40° F. may also be used to increase NMES efficiency, depending upon the local anatomical, physiological, and electrical properties of tissues in the stimulation region and the treatment goals of the NMES therapy session.

As shown, the percentage of electrical energy that travels through muscle tissue is greater in FIG. 1B than in FIG. 1A (due to the energy guidance field created by cooling element 105), while the percentage of electrical energy that travels through the superficial tissue is less in FIG. 1B than it is in FIG. 1A. The increase in the amount of energy that stimulates the muscle tissue, or which stimulates the nerves innervating the muscle tissue, will increase the amount of muscle contraction. The muscle therefore contracts to a greater degree in FIG. 1B than in FIG. 1A. FIG. 1B illustrates the concept of altering the relative impedance of superficial and muscle tissue in the region between the stimulation electrodes in a way that will cause a greater percentage of the electrical current delivered to the body to travel along a tissue pathway that will produce, or result in, muscle contraction.

Figure 1C:
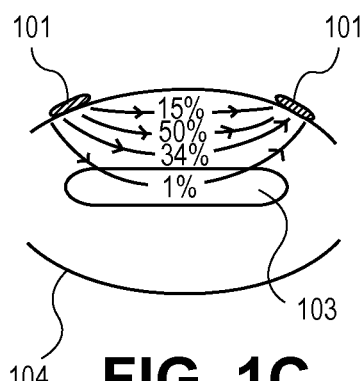
Figure 1D:
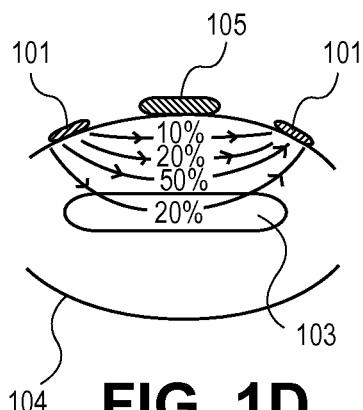

FIG. 1C illustrates a cross-section of an edematous limb 104 with significant tissue swelling. Limb 104 has electrodes 101 positioned similarly to the embodiment shown in FIGS. 1A and 1B. As shown, the distance between the skin surface and muscle 103 is greater than the same distance in the generally healthy limb shown in FIG. 1A. Additionally, short-circuit effects due to excessive ionic fluid may affect the very little (if any) electrical current reaching the deep muscle tissue. As shown, only 1% of the electrical current which is delivered to the limb reaches the muscle. FIG. 1D, compared to FIG. 1C, illustrates the effect that cooling element 105 on the surface of the skin has on the percentage of the electrical current delivered to the body that travels along a tissue pathway that will produce, or result in, muscle contraction. The amount of muscle contraction is greater in FIG. 1D than it is in FIG. 1C. All quantitative information shown in FIGS. 1A-1D is for illustrative purposes and does not necessarily reflect actual functionality of a NMES device applied to a limb surface.

Figure 1E:
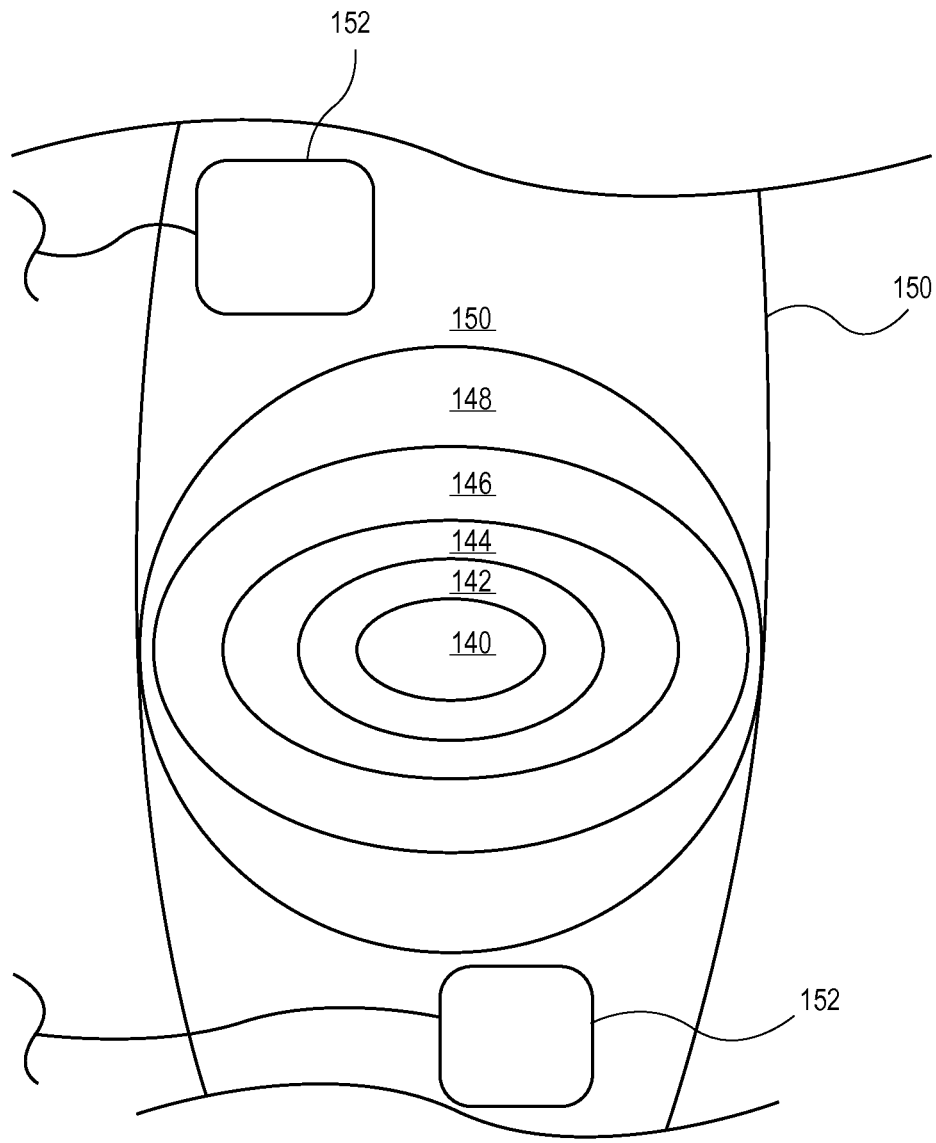

FIG. 1E illustrates a two dimensional temperature gradient on the skin of a portion of leg 150 after a cooling element was placed on the leg for about 7 minutes. The cooling element was placed generally horizontally on the leg, and had a width generally larger than its height, and approximated the shaping of cooling element 204 shown in FIG. 3B. The cooling element was placed substantially in the region indicated as 140 in FIG. 1E. Electrodes 152 are also shown positioned on the leg. The temperature of the skin on the leg was measured after the cooling element was removed. The sizes of the zones indicated are approximations. In zone 140 the temperature of the skin was about 37° F. In zone 142 the temperature was about 42° F. In zone 144 the temperature of the skin was about 57° F. In zone 146 the temperature of the skin was about 72° F. In zone 148 the temperature of the skin was about 85° F. In zone 150 the temperature of the skin was about 87° F. FIG. 1E represents an exemplary temperature gradient after a generally rectangularly-shaped cooling element is placed horizontally between electrodes. Cooling elements with alternative shapes will likely create different temperature gradients, and may in some instances cool the skin that is closer to the electrodes more than that which is discussed in reference to FIG. 1E. For example, one or more of electrodes 152 could be in region 148, 146, 144, or perhaps in some embodiments could even be in zones 142 or 140. While not shown in FIG.

1E, it is understood that the cooling element also creates a temperature gradient through the depth of the leg.

For the NMES therapy systems and methods herein, there is generally no or little cooling effect at the anatomical locations where energy enters or exits the body (i.e., skin upon which the skin electrodes are disposed and closely adjacent thereto), and therefore impedance changes in these regions are minimal or negligible. Energy delivery to and from the body should therefore not be altered significantly because, for example, the impedance in the skin directly adjacent the surface electrodes will not substantially increase. Also, because cooling occurs in precise locations that assist energy transfer to non-superficial muscles, the total path impedance is increased much less than it would be if cooling were applied to the skin over larger anatomical regions (i.e., those that include the electrode locations). Additionally, excessive heat will not generated in the surface electrodes, and thus drying of hydrogel layers should not be accelerated.

FIGS. 1B and 1D illustrate an exemplary embodiment which does not significantly increase skin temperature or tissue impedance on the locations where energy enters or exits the body. As illustrated in FIGS. 1B and 1D, the cooling element is positioned at a location on the skin that substantially avoids a cooling effect at the location of the skin where the electrodes are positioned. Because there is substantially no or very little cooling in the skin to which the electrodes are attached, there is a negligible change in impedance at that location. Electrodes 101 are shown positioned on the skin at a location that is different than the location cooling element 105 is positioned. In particular, in FIGS. 1B and 1D, cooling element 105 is positioned between electrodes 101. By positioning the cooling element between the electrodes, energy transfer in and out of the body remains substantially unaffected.

While the systems and methods of use herein are described as not markedly increasing skin or superficial tissue impedance in the locations where energy enters or exits into the body, in some alternative embodiments the temperature at tissue where energy enters or exits the body can be decreased. The tissue impedance in this region would therefore increase and the energy transfer through the tissue will likely not be as efficient as in embodiments where cooling does not occur where energy enters or exits the body. For example, in FIGS. 1B and 1D, the cooling element could extend over one or both electrodes 101.

As shown in FIGS. 1C and 1D, the application of NMES with tissue cooling can be particularly useful in edematous patients whose tissues may exhibit properties such as the 'short circuit' condition described herein. The systems can, however, also have significant value for healthy or non-edematous persons as well. The systems will allow for more efficient muscle stimulation, which decreases the amount of energy that needs to be to be delivered to the body to produce a given amount of muscle contraction. The reduction in required energy may increase patient tolerance of NMES therapy, in part by reducing the current amplitude reaching superficial nerves (i.e., reduction of the 'pins and needles' discomfort phenomenon). This reduction in energy will also reduce the risk for burns, nerve and/or muscle damage, and other potential complications. The therapies described herein may also be immensely helpful in the NMES treatment of overweight or obese persons (who may be defined by body-mass index), or other persons who require large stimulation energy amplitude to elicit significant muscle contraction. These individuals typically require large stimulation energies to combat the capacitive effect created by excessive adipose located superficial to muscle tissue. For these individuals, the highest energy amplitude allowed by regulatory and/or overseeing body safety standards are frequently required to induce even minimal muscle contraction. As further energy amplitude increases are not an option for these individuals, a more efficient use of the energy that is delivered is imperative to induce effective muscle contraction. Additionally, by reducing inter-patient performance variability, there can be more widespread adoption of the therapies described herein in critical care, skilled nursing facilities, and long-term rehabilitation care settings.

Figure 2:
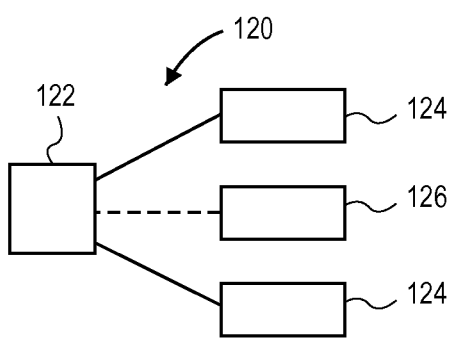
FIG. 2 illustrates an exemplary NMES system.

FIG. 2 illustrates an exemplary schematic representation of a NMES therapy system 120 including stimulation control unit 122, surface electrodes 124, and cooling element 126. Stimulation control unit 122 creates stimulation energy pulses and delivers them to surface electrodes 124, which deliver electrical energy into and out of the body. Cooling element 126 is adapted to apply thermal energy to the body in a region between and/or surrounding surface electrodes 124. Control unit 120 communicates with surface electrodes 124 in a manner suitable for transmitting and receiving electrical signals, such as with a standard cable connection, a wireless connection such as Blue-tooth, WiFi, RF, infrared, optical, acoustic, or other suitable type of connection. In some embodiments the control unit is in communication with cooling element 126. Control unit 122 is a housing separate from electrodes 124, and can be positioned a distance from the person receiving therapy on whom the electrodes are positioned. In alternate embodiments, the control unit may be integrated into a housing unit which includes the stimulating electrodes and/or cooling element. In some embodiments the stimulation electrodes are housed in a custom stimulation pad such that the electrode layout and configuration is optimized for a particular region of the body.

An exemplary method of using NMES therapy systems referred to generally in FIGS. 1 and 2 will now be described. Methods of using the systems described herein may include one or more of the following steps, and may perform them at any suitable time during the therapy procedure. The order of the following steps is in no way intended to be limiting. The exemplary method provides for a more efficient transfer of electrical energy to deep-lying muscle tissues while minimizing the increase in the degree of heat generated in skin electrodes. At least two electrodes are placed on the surface of the skin in the vicinity of a muscle to be stimulated. Cooling energy is applied to skin tissue in a region between and/or surrounding the stimulation electrodes. The application of the cooling energy creates a temperature gradient in which the temperature of the skin and superficial tissue is lowered from their normal temperature to a greater extent than the temperature of deeper-lying tissue (e.g., muscle) is lowered from its normal temperature. Stimulation energy is then applied through the subject by applying stimulation energy to the surface electrodes. The stimulation energy is generated and delivered by a stimulation control unit in communication with the electrodes.

In some methods of therapy, it is not required to simultaneously apply surface cooling and electrical stimulation. For example, superficial tissue may first be pre-cooled by a predetermined temperature or for a predetermined amount of time, after which the thermal stimulus is removed. The temperature gradient will begin to decay at a given rate once the thermal stimulus is removed. Experience suggests that the re-warming rate of the body part is relatively slow, and it could take as long as about 30 minutes or more for a large body part such as the thigh to regain its pre-cooled temperature distribution. During the re-warming period, the NMES performance would be improved by some degree without the need for simultaneous cooling. This particular embodiment of the method is a further example of how known therapies have not recognized the benefit of combining temperature gradients with muscle stimulation.

In some methods cooling is administered intermittently. In these embodiments, surface cooling has "on" periods and "off" periods. For example, during a 60 minute NMES session, cooling energy can be applied every 10 minutes for 5 minutes. One advantage of intermittent cooling is that after superficial tissue temperatures are lowered enough to cause effective changes in tissue impedance, surface cooling can be discontinued, which can prevent skin temperatures from cooling to the extent that the thermal stimulus becomes uncomfortable, intolerable, or unsafe to the person receiving NMES.

Figure 3A:
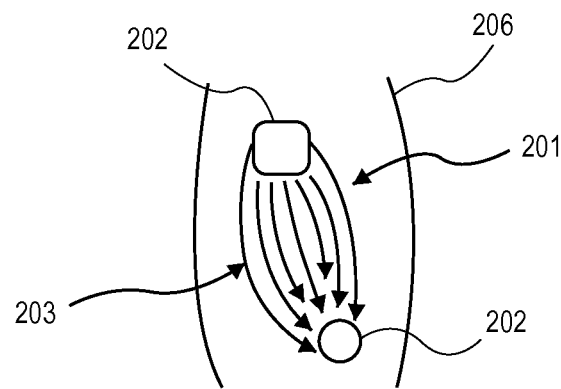
FIG. 3 illustrate the effect that cooling superficial tissue has on the paths that current takes through tissue.
Figure 3B:
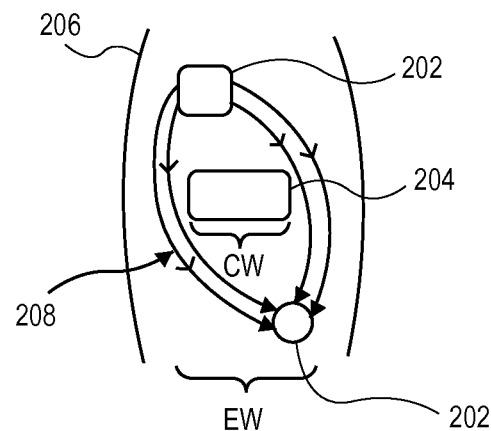
Figure 3C:
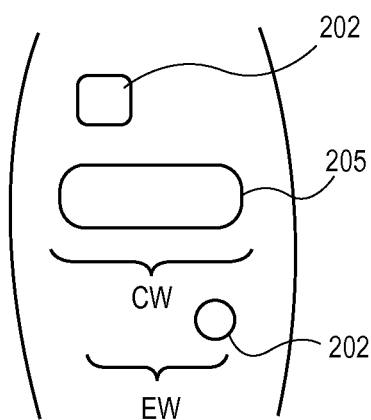

In general, the surface tissue is cooled to increase the impedance of the surface tissue and superficial tissue in order to divert a greater percentage of the electrical energy entering the body to non-superficial muscle tissue (e.g., deep-lying muscle). One goal is therefore to increase the amount of energy that travels along a deeper path and decrease the amount of energy that travels along a shallow path (i.e., a path closer to the surface). As current travels from one electrode to another, however, a large percentage of the energy (or a larger percentage of energy than that which is desired) may travel along or in close proximity to the surface of the skin if the cooling effect is limited to a small region of skin, or if the cooling does not adequately reduce the temperature of the surface of the skin. FIG. 3A illustrates an example of this by illustrating a top-view of low impedance superficial current pathways between two surface electrodes during NMES. In FIG. 3A electrodes 202 are positioned on the surface of skin 206 in stimulation region 201. A distribution of energy pathways 203 illustrate the path current may take when flowing between electrodes 202 under normal conditions. In FIG. 3B cooling element 204 is positioned between electrodes 202. Cooling element 204 has a width "CW" that is similar to a width that electrodes 204 span, "EW." Cooling element 204 eliminates many of the low impedance superficial energy pathways, although some may remain. FIG. 3B shows current paths 208 that exist where low impedance superficial tissue pathways were not eliminated because the cooling effect from cooling element 104 does not sufficiently cool the superficial tissue to increase the impedance sufficiently. Current paths 208 arc around the cooler tissue region. FIG. 3C illustrates cooling element 205 width "CW" that is wider than the width the electrodes span, "EW." The region of superficial cooling is wider (along the transverse plane) than the width of the stimulation electrode distribution. Width CW increases tissue electrical impedance over a large area and thus eliminates nearly all of the low impedance superficial energy pathways. In FIG. 3C current pathways exist below the surface of the skin (not shown). In FIG. 3C, the region of cooling-induced impedance change is sufficient to minimize or even eliminate the existence of superficial low-impedance electrical pathways that arc around the cooled region of tissue.

The size, shape, configuration, etc., of the cooling element can therefore have an affect on the temperature gradient and the degree to which superficial tissue impedance in the stimulation area is altered.

In some embodiments, however, the cooled tissue region may have a width that is similar to the width of the electrode distribution, or even less than the width of the electrode distribution. The width of the cooled tissue region can depend on the local electrical characteristics of the tissue and/or the treatment goals of the NMES therapy session.

Figure 4A:
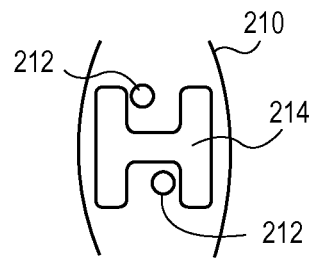
FIG. 4 show exemplary cooling elements.
Figure 4B:
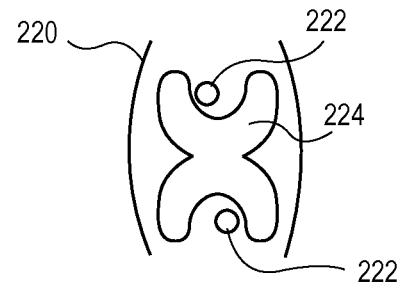
Figure 4C:
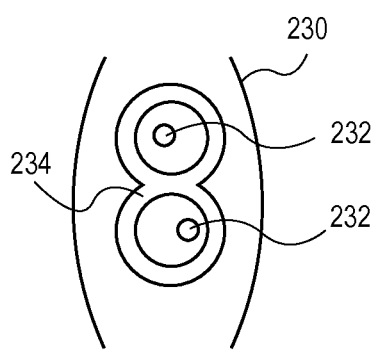
Figure 4D:
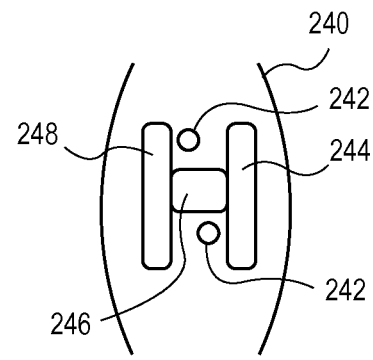

FIGS. 4A-4D show alternative configurations of exemplary cooling elements which are positioned between and at least partially surrounding the electrodes. In the figures, the electrodes have reference numbers 212, 222, 232, and 242 respectively. In FIG. 4A, cooling element 214 is substantially "H-shaped" and placed on skin 210 to minimize the superficial low impedance electrical pathways. In FIG. 4b, cooling element 224 with a shape which mimics two integrated "U" shapes is positioned between and partially surrounding electrodes 224 on skin 220. Cooling element 224 could alternatively be two distinct cooling elements positioned on the skin in the configuration shown in FIG. 4B. In FIG. 4C, cooling element 324 has a substantial FIG. 8 configuration and is positioned on skin 230 between and surrounding electrodes 232. Cooling element 234 could alternatively be two "O" shaped cooling elements positioned on the skin in the configuration shown in FIG. 4C. FIG. 4D shows the "H-shaped" cooling element in FIG. 4A as three discrete cooling elements, 244, 246, and 248 positioned on skin 240 between electrodes 242. Alternative configurations, shapes, and sizes of cooling elements may also be used.

Figure 5:
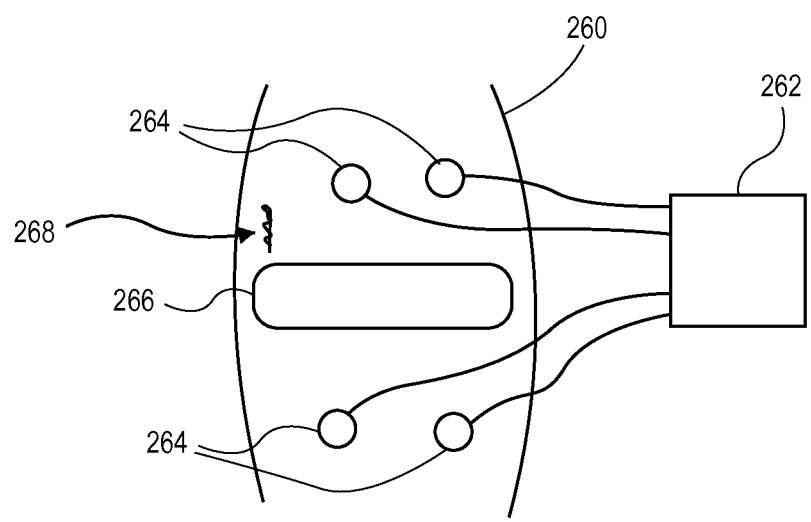
FIG. 5 shows discrete electrodes and a cooling element.

In some embodiments the system includes a plurality of electrodes and a cooling element that are discrete elements and not coupled to one another. The electrodes and cooling elements are, in these embodiments, secured to the skin as separate elements. FIGS. 3 and 4 show such embodiments. The electrodes themselves may also be uncoupled from one or more other electrodes. FIG. 5 shows a plurality of discrete electrodes 264 placed on skin 260. Electrodes 264 are in electrical communication with control unit 262 by leads. Cooling element 264 is not coupled to electrodes 264. Electrodes which are not coupled to the cooling element and/or each other can be useful in patients with abnormal pathology or who have other simultaneous medical interventions that would prevent the use of a pre-manufactured stimulation pad as described below. For example, electrodes 264 and cooling element 266 can be positioned on skin 260 to avoid a broken region of skin 268 (although broken skin is not a contraindication to NMES therapy in general). The use of discrete surface electrodes and cooling element(s) enables an NMES operator to place the stimulation system components in safe and effective locations that are tailored to the needs of the individual.

In some embodiments one or more electrodes are coupled together in a single housing, or pad (and may also be referred to herein as a patch), while in some embodiments one or more electrodes are housed with one or more cooling elements in a single housing, or pad. In some embodiments the systems include custom stimulation pads that have surface electrodes placed in predetermined configurations on the pad. Any number of electrodes can be included in the stimulation pad. A custom stimulation pad can also be configured with a built-in cooling element, or it can be configured such that a detachable cooling element can be easily attached, connected, or used in conjunction with the stimulation pad. These embodiments can assist the NMES operator in applying the surface cooling in the optimal location to increase the efficiency of energy delivery to deep muscle tissues. A stimulation pad can also be configured such that individual electrodes can be detached from the pad.

In some embodiments the stimulation pad is comprised of a thin and flexible housing with an adhesive hydrogel backing to facilitate maintenance of skin contact. The hydrogel backing will also enhance the coupling of electrical energy and signals between stimulation electrodes and the person's body.

In an exemplary embodiment of a system with a stimulation pad, the stimulation electrodes are arranged in a configurable array. The array is configurable such that, at any given time, only a subset of the electrodes in the array are actively delivering energy to a person receiving NMES. However, electrodes inactive for energy delivery may still be configured to deliver relevant information (such as the electrical impedance between it and a second electrode in the array) to the control unit, described in more detail below.

Figure 6:
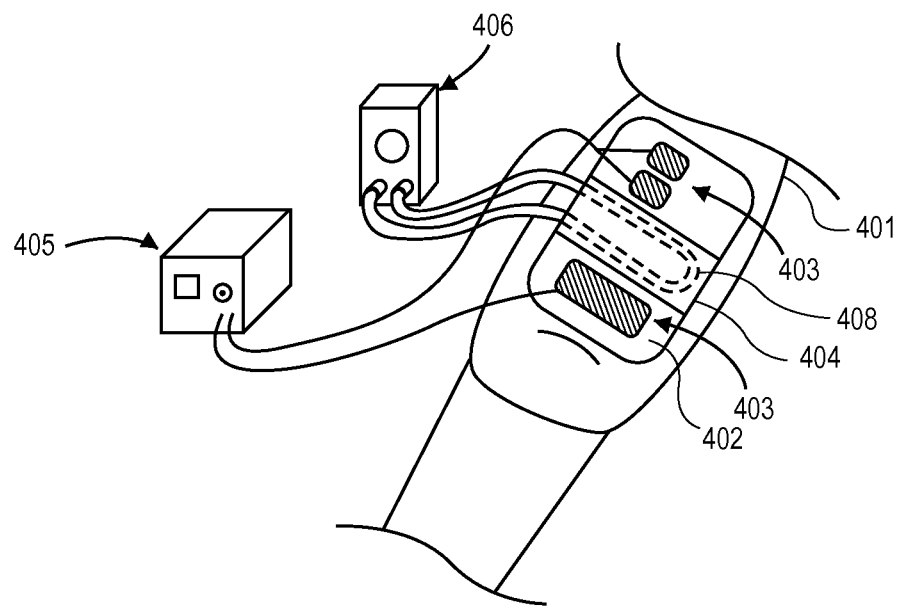
FIG. 6 illustrates a stimulation pad with a cooling element comprises a fluid lumen.

FIG. 6 illustrates an exemplary embodiment of an NMES system including a stimulation pad positioned on a thigh region of leg 401. Surface electrodes 403 and cooling element 404 are integrated into stimulation pad 402, which is thermally conductive, soft, and flexible. Control unit 405 communicates with the stimulation electrodes via a wired connection to deliver electrical energy to the leg. Cooling element 404 includes a lumen 408 within the pad which is in fluid communication with pump 406. Pump 406 (e.g., a peristaltic pump) is connected via inflow and outflow tubes to the cooling element lumen, and is used to circulate chilled fluid, such as water, saline, air, etc., through the lumen. The fluid can be continuously pumped or it can be intermittently pumped through the cooling element. Although three stimulation electrodes are shown, any number of electrodes greater than or equal to two could be incorporated into the pad. Muscle groups other than those in the leg can be stimulated using the systems and methods described herein.

Figure 7:
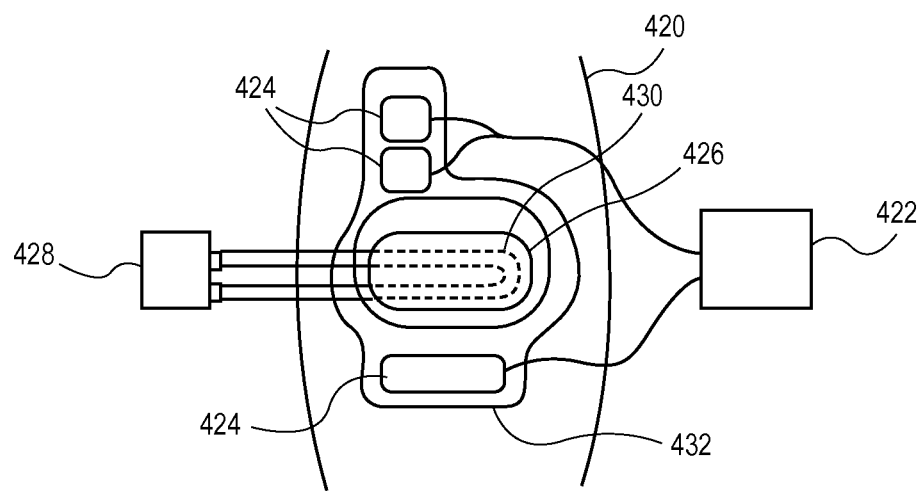
FIG. 7 shows a stimulation pad and a separate cooling element.

FIG. 7 shows an exemplary embodiment in which the system includes a stimulation pad with a cooling element which is not housed in the stimulation pad. In this embodiment, the cooling pad is a separate component that is placed on a person independently of the stimulation pad or stimulation electrodes. Stimulation pad 432 includes a flexible housing that includes stimulation electrodes 424. Electrodes 424 are in electrical communication with stimulation control unit 422. Cooling element 426 is not attached to simulation pad 432, but has lumen 430 that is in fluid communication with pump 428. Pump 428 can be, for example without limitation, a peristaltic pump. As shown, cooling element 426 is positioned between electrodes 424 thereby cooling superficial tissues and creating a temperature gradient as described herein.

Figure 8:
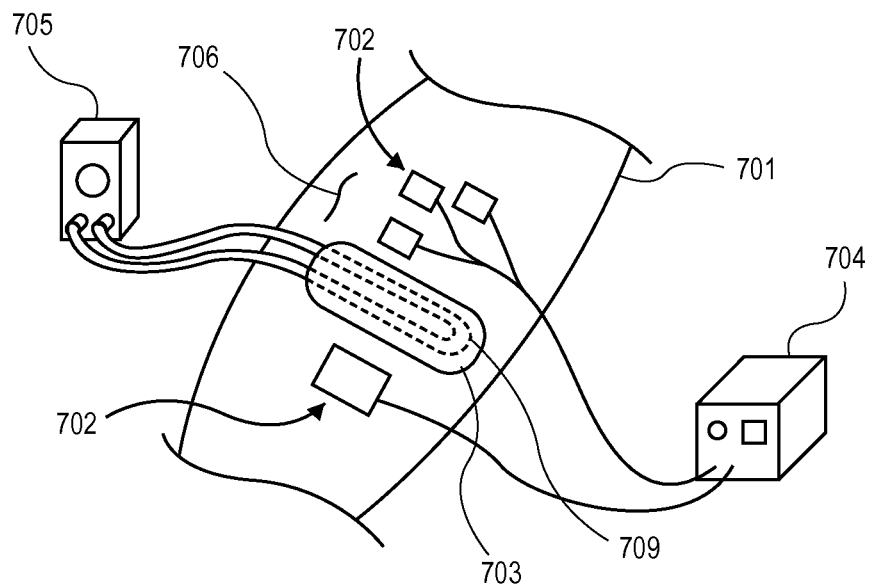
FIG. 8 shows discrete electrodes and a cooling element with a fluid lumen.

FIG. 8 illustrates an exemplary embodiment in which the electrodes are discrete from one another as well as from the cooling element. Stimulation electrodes 702 are positioned independently on leg 701 (although the system can be used on other body parts). Cooling element 703 includes hollow lumen 709 that is in fluid communication with pump 705. Cooling element 703 is used to achieve surface cooling in the region between stimulation electrodes 702. Cooling element 703 is placed on the skin independently of the stimulation electrodes. Pump can pump a chilled fluid through lumen 709, either continuously or non-continuously, and can also include a fluid reservoir.

Figure 9:
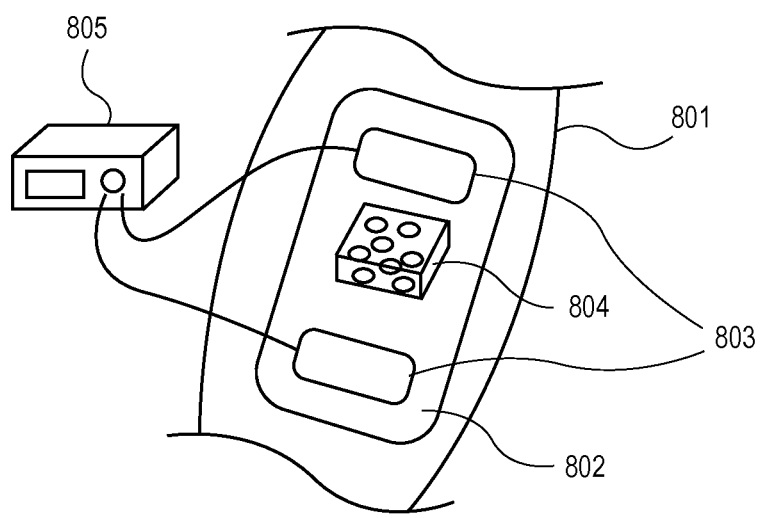
FIG. 9 shows a stimulation pad with an ice pack incorporated therein.

FIG. 9 illustrates an alternative embodiment of a NMES therapy system which includes an ice bath incorporated into a stimulation pad. The system includes pad 802 which includes a fluid-tight and flexible ice water bath 804 in contact with the skin on partial portion of leg 801. Control unit 805 is in wired connection with stimulation electrodes 803, which are also incorporated into pad 802. Both the flexible ice bath and surface electrodes are part of a stimulation pad 802, which fixes the relative positions of the two components of the system in an optimized configuration. The ice bath can alternatively be housed in its own pad, while the electrodes are housed in a separate pad. By using an ice bath, the temperature of the cooling agent (i.e., the ice) will naturally decrease over time as heat is transferred from the patient to the ice. Ice may therefore act as a time-dependent cooling mechanism and may help reduce the "pins and needles" sensation.

Figure 10A:
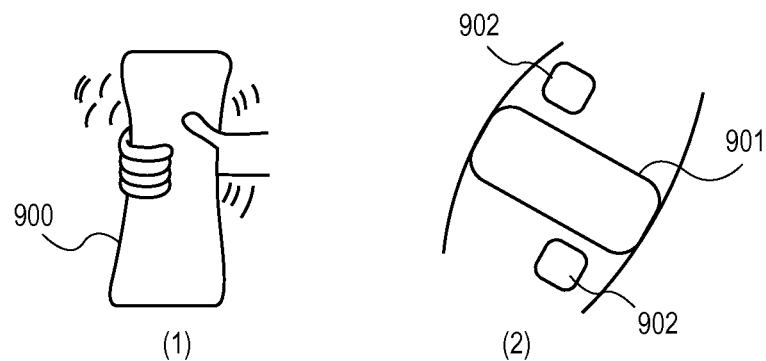
FIGS. 10A-10C show chemical cooling packs.
Figure 10B:
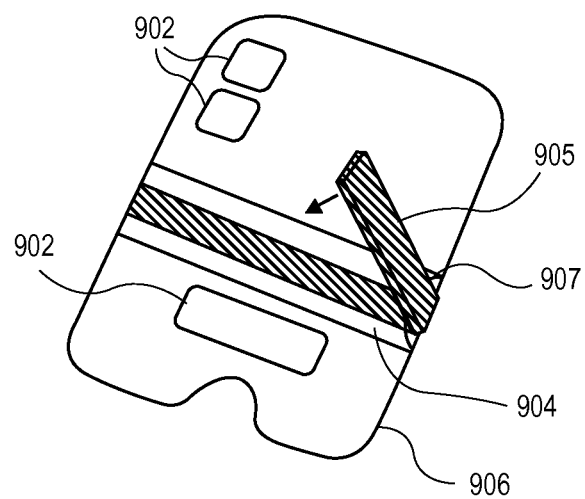
Figure 10C:
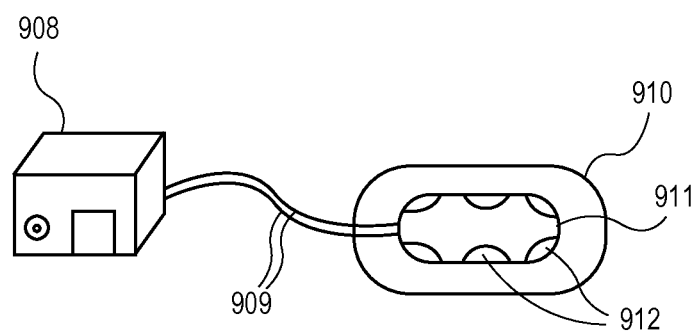

FIGS. 10A-10C illustrate exemplary embodiments of activation mechanisms for a chemical cooling pack to be incorporated with NMES therapy. In FIG. 10A(1), chemical cooling pack 900 is squeezed, thereby breaking an inner lumen to mix chemicals and provide a cold source. In FIG. 10A(2), cold source 901 is placed in the region of muscle stimulation in a location between stimulation electrodes 902. In FIG. 10B, stimulation pad 906 includes stimulation electrodes 902, chemical cooling pack 904, and strap and hook mechanism 905. After positioning the cooling pack in the desired location on the skin, the strap is pulled tight around pivot point 907. Pulling the strap exerts force on the chemical pack 904, breaking an inner lumen and mixing chemicals to create a cold source. The strap is then secured to itself using, for example, a Velcro strap, snap, or other securing mechanism. The cold source is thereafter held in place. In FIG. 10C, the stimulation pad is in electrical communication with control unit 908. A cross-sectional view of the chemical cooling pack is shown. Wires 909 from control unit 908 extend through outer compartment 910 of the cooling pack and connect to resistive heating components 912 secured to inner lumen 911 of the cooling pack. At a desired time, control unit 908 sends electrical signals to resisting heating components 912 via wires 909, which melts portions of the inner lumen, causing the chemicals to mix and thereby create a cold source which can then be applied to the skin.

Alternative embodiments utilize a chemical mechanism to achieve superficial cooling. For example, the stimulation pad may have an open center portion such that the surface between the stimulation electrodes is exposed. After placement of the stimulation pad (or, in some embodiments, after placement of discrete electrodes), a chemical agent is applied on to the exposed surface, reducing the temperature of superficial tissues. The agent can be an agent that can be sprayed or wiped onto the exposed surface. Alternatively, a chemical mechanism may be part of a separate component (e.g., an instant cooling pack), that may be positioned in contact with superficial tissue.

In some embodiments the cooling element can be a thermoelectric element, such as a Peltier device. Peltier devices used for cooling are known. The thermoelectric element can be used to cool the tissue as described herein.

In some embodiments the cooling mechanism can include the use of gas expansion. By decreasing the pressure of gas in a fixed volume, the temperature of the gas decreases and can be used to cool the superficial tissues. In some embodiments the use of gas expansion is incorporated with one or more different cooling mechanisms, such as a circulating fluid, a chemical cooling mechanism, and/or a thermoelectric cooling mechanism.

Figure 11:
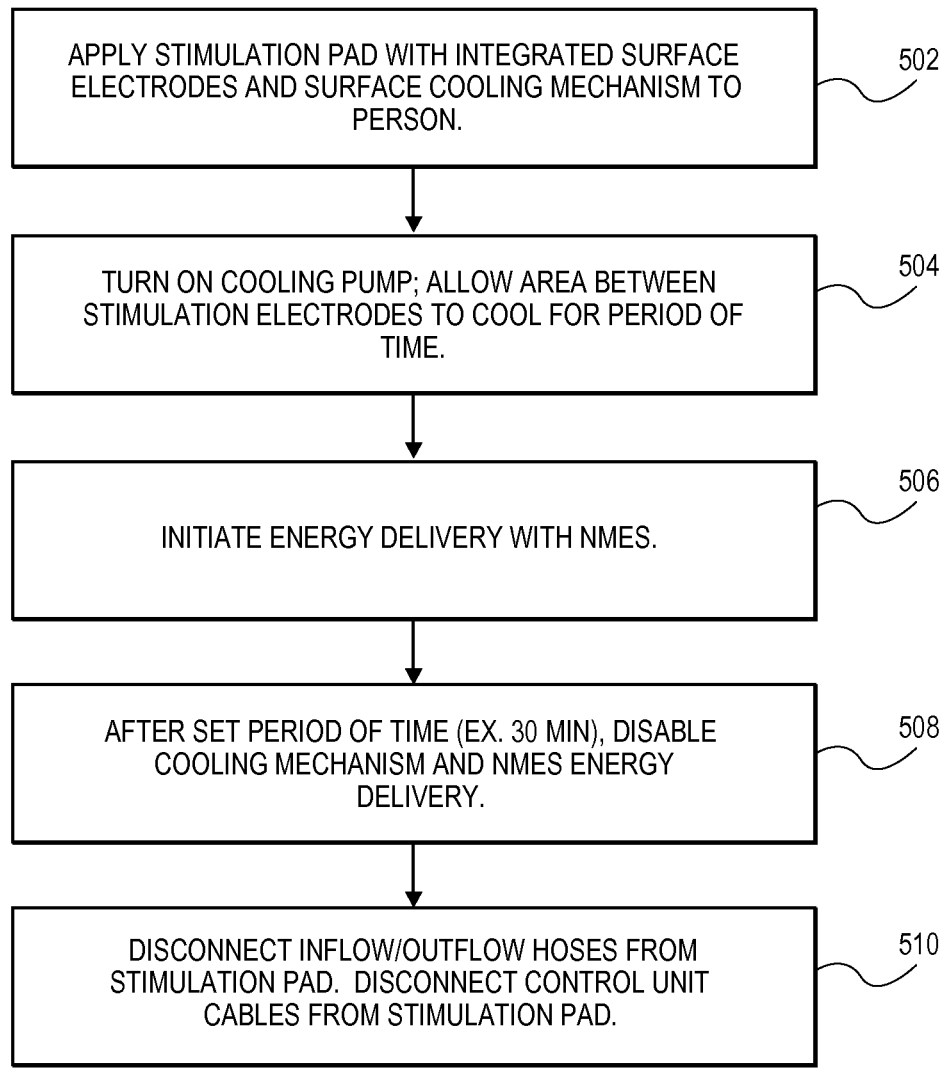
FIG. 11 shows an exemplary method of using a NMES therapy system.

FIG. 11 illustrates a merely exemplary embodiment of a method using a system for NMES therapy. The order of the steps is not intended to be limiting, and some steps need not be performed. Other steps not shown can be included at any suitable time during the procedure. First, stimulation electrodes and a cooling element are applied to the surface of the skin at step 502. The electrodes can be discrete or they can be incorporated into a pad, and perhaps with the cooling element. In embodiments which include a cooling pump, the pump is turned on in step 504 which cools the area between the electrodes for a given period of time. Electrical energy is then delivered to the patient through the electrodes at step 506. After a set period of time (e.g., 30 minutes) the cooling mechanism and NMES energy delivery are discontinued as shown in step 508. Finally, the inflow/outflow hoses are disconnected from the stimulation pad and the control unit is disconnected from the stimulation pad. Any of these steps may be optional or may be interchanged with other steps, or the order of the steps may be varied.

Application of the surface cooling can begin several minutes (e.g., about 5 to about 10 minutes) before NMES energy delivery begins. Depending upon the embodiment of the devices and systems used to apply NMES, surface electrodes are applied to the body either before or after the cooling is initiated. Surface cooling continues during NMES energy delivery. During this period, the temperature of superficial tissues may be held constant, or, in some embodiments, superficial temperature may continue to decrease during NMES. In some embodiments, surface cooling may be used intermittently during the NMES therapy session. Surface cooling may alternatively be implemented only prior to initiating NMES energy delivery. Surface cooling may alternatively be applied to the stimulation region after NMES energy has begun. For example, a 10 minute NMES warm-up period may precede a period of cooling with NMES therapy and/or a period of cooling followed by NMES therapy.

Figure 12A:
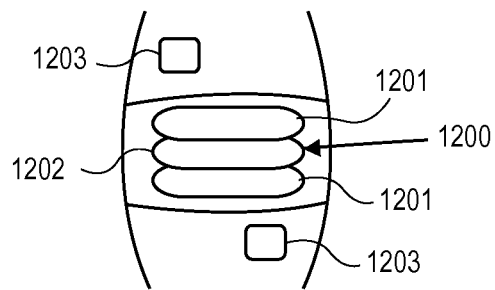
FIGS. 12A-12C show exemplary cooling element with multiple cooling zones.
Figure 12B:
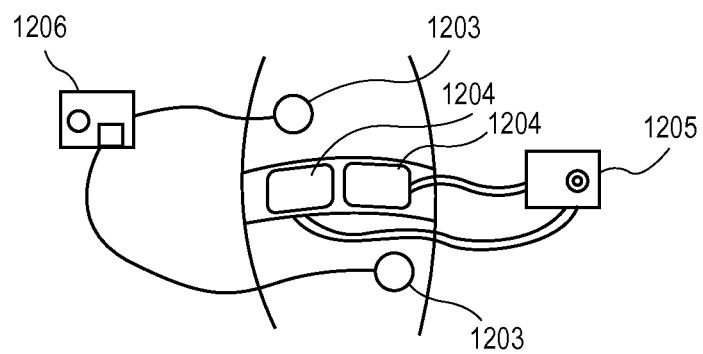
Figure 12C:
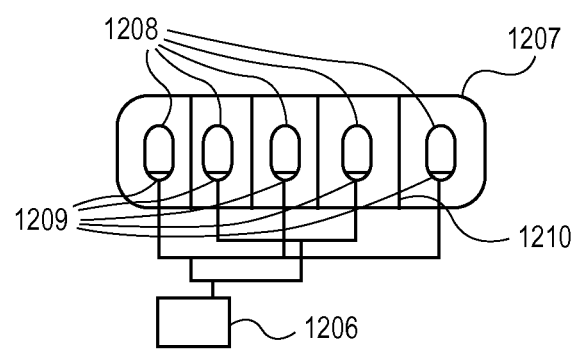

FIGS. 12A-12C illustrate embodiments in which the system includes a cooling element with a plurality of zones, or regions, of cooling. FIG. 12A shows a partial portion of a leg with cooling element 1200 which includes first cooling zone 1201 and second cooling zone 1202. Each of the zones is positioned between stimulation electrodes 1203. Each cooling zone may be controlled independently or dependently of the other zones. That is, the zones can be active or inactive independent of the other zone(s). The zones can be independent or dependently controlled by a control unit (not shown). In FIG. 12B control unit 1206 communicate with electrodes 1203. Pump 1205, driven either by control unit 1206 or independently controlled, circulates a cooled fluid through two or more separate zone housings 1204. The plurality of housings are not in fluid communication with each other. Valves or similar mechanisms can also be used to allow fluid to be directed to each housing individually or through multiple housings simultaneously. The embodiment in FIG. 12C utilizes a chemical cooling pack with multiple cooling zones. Outside compartment 1207 of the cooling pack houses more than one inner lumen 1208 that are sealed, or chemically isolated, from one another by compartmentalization elements 1210 (only one of four is identified). Each inner lumen may be broken by melting a portion of it by delivering energy from control unit 1206 to resistive heating elements 1209. Chemicals in the different zone of the cooling pack can be mixed at any time individually based upon instructions from the control unit.

For NMES therapy sessions expected to last for more than about 15 to about 30 minutes, there may be a concern of skin damage due to extended cold exposure. In some embodiments a first superficial region of tissue is cooled, and then a second, different, superficial region of tissue is cooled. By shifting the cooling regions, some risk of skin damage due to extended cold exposure may be reduced. In some embodiments the second region overlaps the first region. Given the relatively long re-warming time for tissue (after exposure to a cooling element has been discontinued) and extended period of increased NMES efficiency after cooling is removed from an area, adjusting the region of thermal transfer may allow for maintenance of an effective thermal gradient in tissues slightly deeper than the skin while avoiding potential low impedance electrical pathways on the skin surface. In embodiments that use a circulating cooled fluid as the cooling mechanism, the region of cooling may be alternated or changed by selectively opening and closing valves that control the flow of the fluid to certain regions of the cooling element. In embodiments that use a chemical instant cool pack as the cooling mechanism, a cold pack with a two-stage lumen may be used such that chemicals only mix in specific regions at specific times. Initially, the first stage inner lumen of the pack is broken to mix chemicals and cool one area. As the chemical reaction (and thus the cold source) ends in one area, the second stage of the lumen is broken to extend the thermal stimulus to a second area of skin. Variations may be provided using lumens with any number of stages to provide the desired amount and/or timing of thermal stimulus to one or more desired areas of skin. In embodiments that include thermoelectric devices as the cooling mechanism, the control unit may selectively activate specific zones of thermoelectric elements (independently or dependently of one another) by selectively sending energy or signals to each zone. For example, in FIG. 12A cooling zones 1201 and 1202 can be discrete (two or more) thermoelectric devices. The zones can be in communication with a cooling control unit, which is either housed with the stimulation control unit or is in a separate housing. The cooling control unit can be adapted to control the thermoelectric devices such that cooling zones 1201 and 1202 can be set to different temperatures, can be activated for different cooling times, etc. The thermoelectric devices can also have different sizes and shapes.

Figure 13:
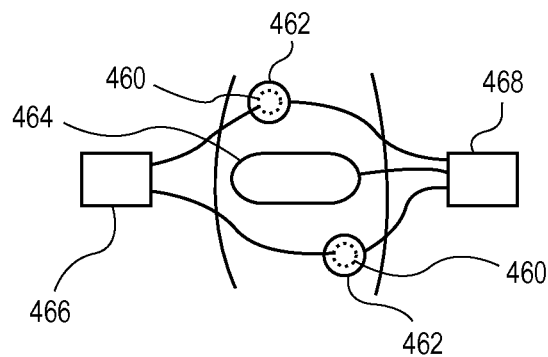
FIG. 13 shows a muscle stimulation system with cooling elements placed over surface electrodes.

In some embodiments different regions, or zones can be subject to different degrees of cooling, which allows for different regions of skin to be subjected to different temperatures. As described herein, it is generally not desirable to excessively cool tissue in the location where energy enters and exits the body (i.e., the location of the surface electrodes) because this increases local impedance and impairs electrode performance and sustainability without enhancing energy delivery to deep-lying muscle and/or nervous tissues. However, in some instances, it may be desirable to mildly cool (for example, on the order of about 1 to about 5° C.) tissue regions in the electrode location (or the electrodes themselves) to provide additional protection against the risk of burns. This mild cooling may provide additional burn protection without substantially raising tissue impedance in the region where energy enters or exits the body. In one or more other spatial zones located between the electrodes used for stimulation, more appreciable superficial cooling (for example, on the order of about 20 to about 30° C.) may be implemented to increase the efficiency of energy transfer to deep-lying muscle and/or nervous tissues. Any of the suitable embodiments described herein which describe a plurality of cooling regions, or zones, can be adapted to provide a plurality of different cooling zones, each of which (or some of which) can have a different thermal effect of different regions of tissue. For example, FIG. 13 illustrates an exemplary embodiment of a system which includes control unit 466 in communication with electrodes 460 (shown in phantom). The cooling element includes first cooling element 462 and second cooling element 464. Pump 468 is in fluid communication with both of the cooling elements. First cooling element 462 includes two discrete cooling elements positioned over electrodes 460. Second cooling element 464 cools the region between electrodes 460 more than first cooling element 462 cools the region (or also the electrodes) near the electrodes. This allows for a milder decrease in temperature in the region where energy enters and exist the body, but provides for a greater degree of cooling between the electrodes.

It may be desirable to maintain a relatively constant cooling temperature during the entire duration of the therapy. In these instances, a circulating cooled fluid, a chemical approach, or a thermoelectric approach may be more beneficial than using a cooling element such as an ice bag or ice bath, as ice will melt be unable to sustain the skin at a constant temperature. There may be additional advantages of the cooled fluid and chemical mechanisms of cooling that are related to workflow. For example, a cooling pump or instant chemical cooling pack can be kept conveniently in a storage area by a patient's bedside, and be activated when needed without requiring time associated with setup and storage that an ice bag or ice pack may require. Additionally, ice bag and/or ice baths may be prone to moisture creation and/or leakage. Different types of cooling elements can therefore be used to adjust the temperature of the cooling element over time.

The cooling element (or at least portions of it) is preferably held in secured contact with the skin. Movement of the region of stimulation caused by voluntary or involuntary muscle contraction or by other sources of motion could shift the position of or dislodge the cooling element from direct and efficacious thermal contact with superficial tissues. Some embodiments of the system therefore maintain desired thermal contact between the cooling element and the superficial tissues, even when such motion occurs.

Figure 14A:
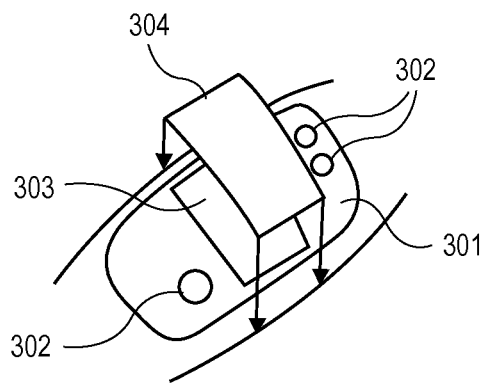
FIGS. 14A-14C show embodiments that allow for a cooling element to be held firmly in place in the region of stimulation.
Figure 14B:
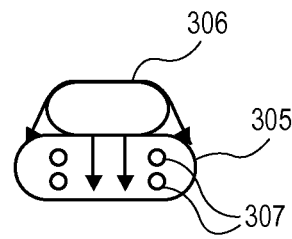
Figure 14C:
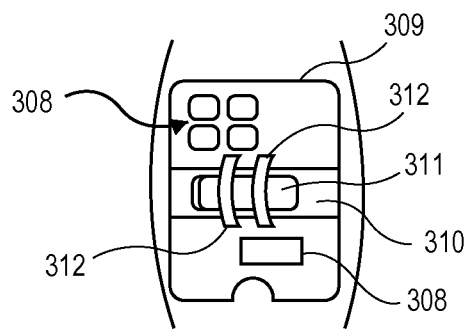

FIGS. 14A-14C illustrate embodiments of tightly securing the cooling element to the skin. In FIG. 14A stimulation pad 301 includes three stimulation electrodes 302, cooling element 303, and weight 304. In one embodiment the weight is flexible and is similar in mass and flexibility to a sandbag. Cooling element 303 is positioned on the desired region of the skin and weight 304 is positioned atop the cooling element. Weight 304 secures cooling element 303 in place against the desired region of skin. In FIG. 14B, weight 306 sits atop cooling element 305 and is attached thereto using connectors 307, which are in the form of snap connectors. Other types of connecting elements may be used. In FIG. 14C, stimulation pad 309 comprises built-in stimulation electrodes 308 and a built-in cooling element 310. Weight 311, which can be flexible, sits atop cooling element 310 to exert downward pressure, and is held in place with the use of straps 312 that are adapted to couple to the stimulation pad on either side of the weight/cooling mechanism assembly. Alternative mechanisms of applying pressure to the cooling element may be used to maintain the cooling element is secured contact with the skin.

Tightly securing the cooling element to the skin may both maintain the cooling mechanism in a desired position as well as provide a tight seal between the cooling mechanism and the skin surface to minimize the build-up of moisture in the stimulation region. Alternative embodiments may include the use of mild adhesives or circumferential straps for maintaining the placement of the cooling element.

In some embodiments the NMES therapy system includes a way to prevent or minimize moisture from forming on the surface of the skin. When warm air comes in contact with a colder surface, moisture from the air may condense on the colder surface. Moisture on the skin surface may decrease the electrical impedance of the skin and also may pose a safety hazard during energy delivery. In some embodiments the pad on the skin includes several layers to avoid excess skin moisture during NMES with surface cooling. For example, in one embodiment the cold source is an inner layer contained within a compartment that is surrounded by a middle absorptive layer that may be thin enough so as not to serve as a thermal insulator. The middle layer can be a material similar to a paper towel, foam, or other suitable material. A thin outer layer that makes contact with the skin is comprised of non-absorptive material and surrounds the middle layer. The outer layer prevents moisture from forming on the surface of the skin.

In alternative embodiments, moisture build-up in the region of stimulation may be reduced by preventing warm air from reaching the cold source/skin interface, which can be accomplished by reducing or eliminating the air between the cooling element and the skin. Suction and/or vacuum pumps can be used remove the air. Applying sufficient pressure on the cooling element can also reduce the amount of air for circulation. Weights, straps, or other devices can be used to apply pressure to the cooling element.

In general, the NMES therapy systems have a stimulation control unit in communication with the surface electrodes that generates electrical energy and delivers it to surface electrodes. In general, the control unit has a power source (e.g., a battery or isolation transformer for use with mains power), and can include any of the following: hardware components, software components, a voltage/current amplifier, a microcontroller, FGPA, timing circuitry, waveform generation circuitry, signal processing circuitry, and memory. In some embodiments the primary operation of the control unit can be provided by a microprocessor, field programmable gate array (FPGA), application specific integrated circuit, some combination of these mechanisms, or other suitable mechanism. When activated, the control unit generates electrical stimulation signals that are transmitted to the surface electrodes, which couple the energy into the body to stimulate muscle tissue.

Parameters of the electrical stimulation can be established prior to stimulation, and the control unit can be adapted to allow stimulation parameters to be adjusted at any time before, during, or after stimulation therapy. Parameters can be adjusted manually or the control unit can be configured such that parameters are adjusted automatically, which can occur according to a pre-established therapy protocol, or based on feedback signals monitored and sensed from the patient, discussed more below. Exemplary electrical stimulation parameters include, without limitation, the duration of therapy, stimulation pulse energy amplitude, etc.

In some embodiments the control unit includes a user interface to allow medical personnel to control the parameters of electrical energy delivery to the patient. The control unit can be adapted to allow a user to manually set (i.e., establish) the parameters of electrical stimulation, or it can be adapted to allow a user to adjust the parameters of electrical stimulation at any point during or after the therapy. The user interface can be housed in the control unit, or it can be a separate device similar to a remote control that is in communication with the control unit. The user interface can include buttons, knobs, dials, switches, etc., to control the parameters of energy delivery. The user interface may also include functionality to allow the user to test the operation of the control unit or any other component of the system to detect any errors or malfunctioning components.

In some embodiments the control unit is configured to automatically adjust stimulation parameters based on optimization software in the control unit.

In some embodiments the control unit is configured to receive sensed patient signals that are generally sensed using one or more sensors positioned on or within the patient. One or more sensors can be used to sense parameters from the subject and provide feedback to the control unit.

In some embodiments the sensor can include a temperature sensor configured to monitor the temperature on the skin of the patient. The control unit can be configured to continuously or periodically receive the sensed temperature and a control algorithm can compare the sensed temperature with a reference temperature to determine if the sensed temperature is higher or lower than the reference temperature. Based on the comparison, the therapy may require that the cooling element be activated, deactivated, or adjusted to increase or decrease the temperature of the skin. The degree of cooling can be adjusted manually, or the control unit can have software built-in to modify the cooling protocol to control the skin temperature. Monitoring the skin temperature can provide an indication of the temperature gradient created in the tissue and therefore provide an indication if the gradient is sufficient to deliver a sufficient percentage of energy entering the patient to deep-lying muscle tissue. Thus, temperature is an exemplary patient parameter than can be sensed to control the amount of surface cooling by the cooling element, examples of which are described herein In some embodiments the sensor includes a sensor to sense the degree of muscle stimulation, or contraction. Sensing muscle contraction can be performed with, for example without limitation, an EMG. When the sensor is adapted to sense muscle contraction, the sensed parameter can be any parameter indicative of the amount of muscle contraction. The control unit can be adapted to receive the sensed parameter indicative of muscle contraction and use this information to control the operation of the cooling element or to control the electrical stimulation. For example, if the sensed parameter indicative of muscle contraction indicates an insufficient amount of contraction, it may be desirable to either increase the cooling effect on the surface of the skin (to increase the superficial skin impedance) or to increase the amount of electrical stimulation, or a combination of the two. The response to the sensed parameter can be a manually adjusted (e.g., via a user interface) or it can be automatically controlled by the control unit. Some exemplary muscle sensor that can be incorporated into the NMES therapies described herein can be found in application Ser. No. 12/497,230, filed Jul. 2, 2009, which is incorporated by reference herein.

In some embodiments one or more sensors are coupled to the person receiving NMES and are adapted to record data indicative of muscle contraction, and feedback control systems within the control unit are used for closed-loop optimization of stimulation energy waveforms.

The control unit can be configured to activate a cooling element. In one exemplary embodiment, local tissue cooling in the stimulation region is initiated after several minutes of "warm-up" stimulation energy is applied to the subject. It may be beneficial if the system does not require a care provider to return and make adjustments after the "warm-up" stimulation energy such that cooling is automatically initiated at a pre-established time during a therapy procedure.

In embodiments that use a circulating cooled fluid (examples of which are described herein) to create a temperature gradient, the control unit can be in communication with a pumping element that controls the flow of fluid to the cooling element. The control unit therefore controls the skin temperature of the patient. The control unit can be adapted to activate the cooling mechanism at a predetermined time or at a feedback determined time.

Other embodiments use an instant chemical cooling pack (such as urea-based or ammonium-nitrate/water packs that are commercially available) that activates when an inner lumen is broken, causing two substances to mix and chemically react. Examples of such embodiments are described herein. Electrical current generated in the control unit can be used to melt or break predetermined regions of the inner lumen of the cooling pack, causing the substances to mix.

The control unit can also include one or more memory units to store, for example without limitation, algorithms used to carry out the functionality of the NMES therapy, therapy protocols, sensed patient parameters, stimulation parameters, and/or cooling parameters. The memory can be in any of the following forms: RAM, ROM, EEPROM, volatile memory, non-volatile memory, or any combination thereof. The memory units can be in communication with a processor to carry out the NMES therapy.

One or more processors in the control unit can be coupled to a clock for timing and synchronizing various aspects of the therapy.

The control unit can also include a communication interface adapted to communicate with a remote device such as, for example without limitation, a personal computer or a network to provide for communication of data, programming commands, etc. Communication can be carried out using conventional wireless protocols, such as telemetry, inductive coil links, RF links, other electromagnetic links, magnetic links, infrared links, optical links, ultrasound links, etc. The communication interface can include both a receiver and a transmitter to allow for two-way communication so as to allow for providing software updates to the control unit, transmit stored or real-time data, transmit inputs from medical personnel, etc.

The control unit can be used to control various aspects of the therapy even if not specified described herein. The control unit may be a single housing or it may be more than one housing, any number of which are in communication.

Figure 15:
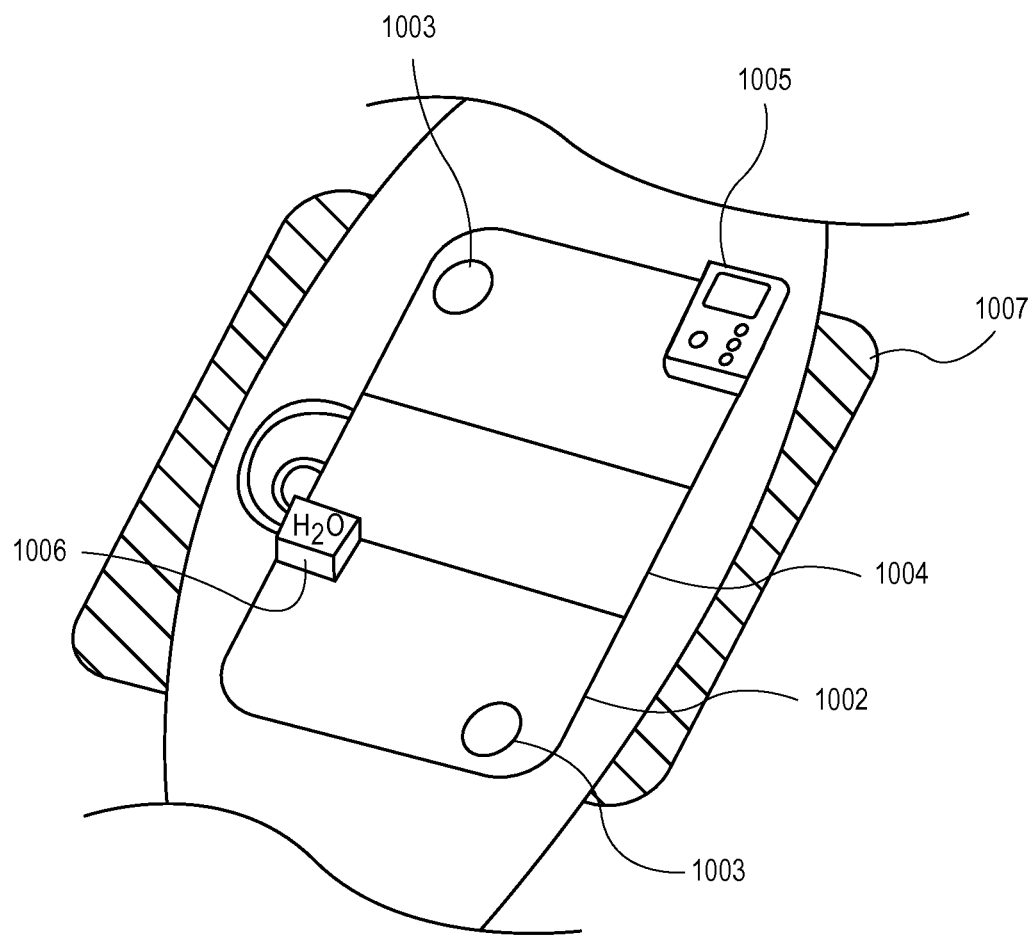
FIG. 15 shows an embodiment with an optional heating element disposed on a posterior portion of a leg.

In some embodiments the systems include a heating element in addition to a cooling element. While the cooling element is used to decrease the temperature of tissue, the heating element is used to increase the temperature of issue. In FIG. 15 heating element 107 is positioned on the posterior side of leg 1001 (or the leg presses against the heating element when the patient is lying on a table), while stimulation pad 1002 is positioned on the anterior portion of leg 1001. Stimulation pad 1002 includes cooling element 1004 and stimulation electrodes 1003. Control unit 1005, as well as and pump and fluid reserve 1006 are also incorporated into stimulation pad 1002. Surface cooling is applied by cooling element 1004 as described herein. Heating element 1007 is positioned to apply surface warming near the hamstrings and/or gluteals, although the system can be applied to other muscles. The posterior warming acts synergistically with the anterior surface cooling to increase the temperature gradient between deep-lying muscle tissue and superficial tissues on the anterior side of the leg, increasing the efficiency of electrical current deposition to muscle tissues. Secondly, the warming can help maintain core body temperature within normal levels. Prolonged surface cooling may change temperatures near large blood vessels, which may in turn cool blood and thus lower internal core temperature. A posterior heating element may help offset any cooling induced changes in core temperature by warming tissues near large vessels, without decreasing the temperature gradient on the anterior portion of the leg. The warming element can be coupled to its own control unit to control the temperature of the heating element. The warming element can be similar to a heating pad.

Figure 16A:
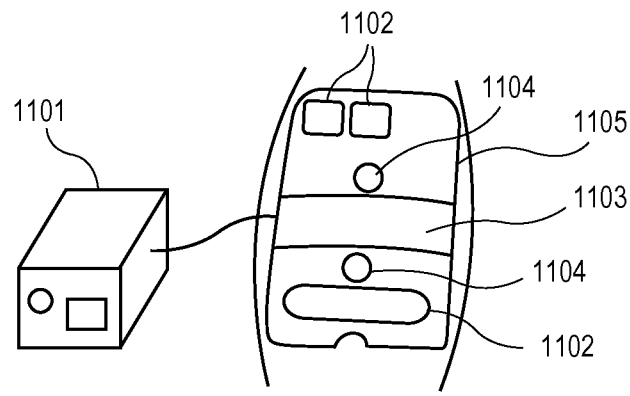
FIGS. 16A-16C show an embodiment with an ultrasound transducer.
Figure 16B:
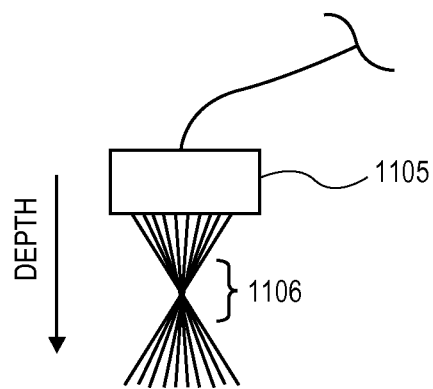
Figure 16C:
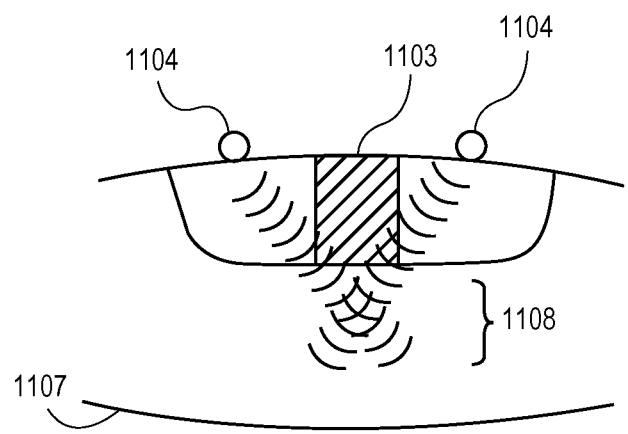

FIGS. 16A-C illustrate alternate embodiments which comprise an ultrasound transducer. In FIG. 16A, control unit 1101 is in electrical communication with stimulation pad 1105, which includes stimulation electrodes 1102, cooling element 1103, and two ultrasound transducers 1104. FIG. 16B shows the acoustic energy distribution from focused ultrasound transducer 1105, with the peak spatial distribution of energy in the beam occurring in the focal region 1106. Tissue heating may occur primarily in the focal region, as in other regions the energy is too spread out spatially to significantly raise temperatures. FIG. 16C is a cross-sectional side view of limb 1107 being treated with NMES therapy. Ultrasound transducers 1104 transmit acoustic energy from the surface of the skin through superficial tissues, with a focus in deeper regions of tissue 1108.

Operated by the control unit or other control device, transducers may use relatively low frequency ultrasound energy (e.g., from about 1 to about 4 MHz) with an electronic and/or concave lens focus to a depth appropriate for the muscle group being stimulated. Ultrasound energy may be partially absorbed by tissue through which it propagates, and this energy may be converted to heat. Due to the focal nature of ultrasound, it is possible to deposit the overwhelming majority of the energy in the focal region while depositing minimal energy in more superficial regions of tissue. Accordingly, deeper tissues in the focal region may be warmed without significant warming of superficial regions. This method may strengthen the thermal gradient that is produced by the superficial cooling mechanism, as well as help ensure that the core body temperature does not drop too low.

EXAMPLE

A research study has investigated the NMES therapy with skin cooling disclosed herein. Twenty healthy volunteers were recruited. The first group (Group 1) of ten volunteers included all-comers (median age 44 years, range 22-70 years, median BMI 25.0, range 22.0-38.3). The second group (Group 2) of volunteers consisted entirely of clinically obese (BMI>30.0) individuals (median age 53 years, range 25-75 years, median BMI 32.4, range 30.1-39.6). An additional research study that recruits critically ill patients is underway, and preliminary results are available.

In the first study, volunteers had their posture stabilized and muscle stimulation electrodes were applied in a mirror image configuration on each thigh in the region of the quadriceps. A medical dynamometer was placed over each ankle. During muscle stimulation, the quadriceps contracts, causing the leg to extend. The medical dynamometer reads this leg extension force. Leg extension force for a fixed (constant) amount of stimulation energy is a proxy for the number of muscle motor units recruited during stimulation with that amount of energy, and thus serves as a good descriptor of muscle stimulation efficiency. After baseline measurements of muscle strength in each leg were made, one leg was randomly chosen to receive an ice bag placed on it in the region between stimulation electrodes, while on the other leg a room-temperature control bag was placed. Measurements of leg extension force were made in each leg at 3 minute intervals. After 20-30 minutes of cooling, both ice and control bags were removed from the legs, and measurements were continued during the re-warming period.

In the study, muscle stimulation was provided as a pulse train composed of a series of asymmetric, biphasic square waves with pulse durations of 300 microseconds and at repetition rates of 40 Hz. Pulse trains lasted for 5 seconds with 1 second energy ramp up and ramp down times (i.e., 3 seconds of maximum energy delivery), and were followed by resting periods of at least 10 seconds. The maximum current delivered by each stimulator channel to each individual ranged from about 30 to about 80 mA.

In some embodiments the frequency content of the individual pulses is about 10 kHz or lower. In some embodiments it may be about 5 kHz, while in some embodiments it may be about 1 kHz. In some embodiments the pulse repetition rates are about 30 Hz or greater. In some embodiments the pulse repetition rates are between about 30 Hz to about 50 Hz. In some embodiments the energy is delivered with an alternating series of on (during which pulses are applied at a given repetition rate) and off times (during which no pulses are applied). In some embodiments the on times last for about 5 seconds to about 10 seconds. In some embodiments the off times last for about 10 seconds to about 20 seconds.

This study showed the immense usefulness of the systems and methods described herein. Leg extension force (and thus muscle stimulation efficiency) increased in the experimental leg during the cooling period in all 20 volunteers. The average peak increase in extension force from baseline achieved with superficial cooling in the experimental leg was 69.9% in Group 1 and 94.8% in Group 2. This larger increase in the clinically-obese group shows the extreme efficacy of the NMES therapy with cooling for improving results in challenging stimulation cases (i.e., persons who generally require the maximum energy allowed by regulatory and/or overseeing body safety standards is required to achieve even mild muscle contraction). The large increase in Group 2 is especially significant because it allows for muscle contraction to go from a level that is not strong enough to prevent atrophy, to one that is useful for preserving muscle strength and improving functional outcomes. Accordingly, the presently disclosed devices, systems, and methods will enable this group of individuals to receive significant or improved benefit from NMES therapy.

Relative to the control leg, the mean 9-minute average increase in extension force achieved with superficial cooling in the experimental leg was 52.6% relative to baseline, indicating that increases in stimulation efficiency are sustainable over a significant period of time. Overall, muscle contraction strength increases achieved with superficial cooling were determined to be extremely statistically significant ($p<0.0001$) with a paired t-test analysis.

Figure 17:
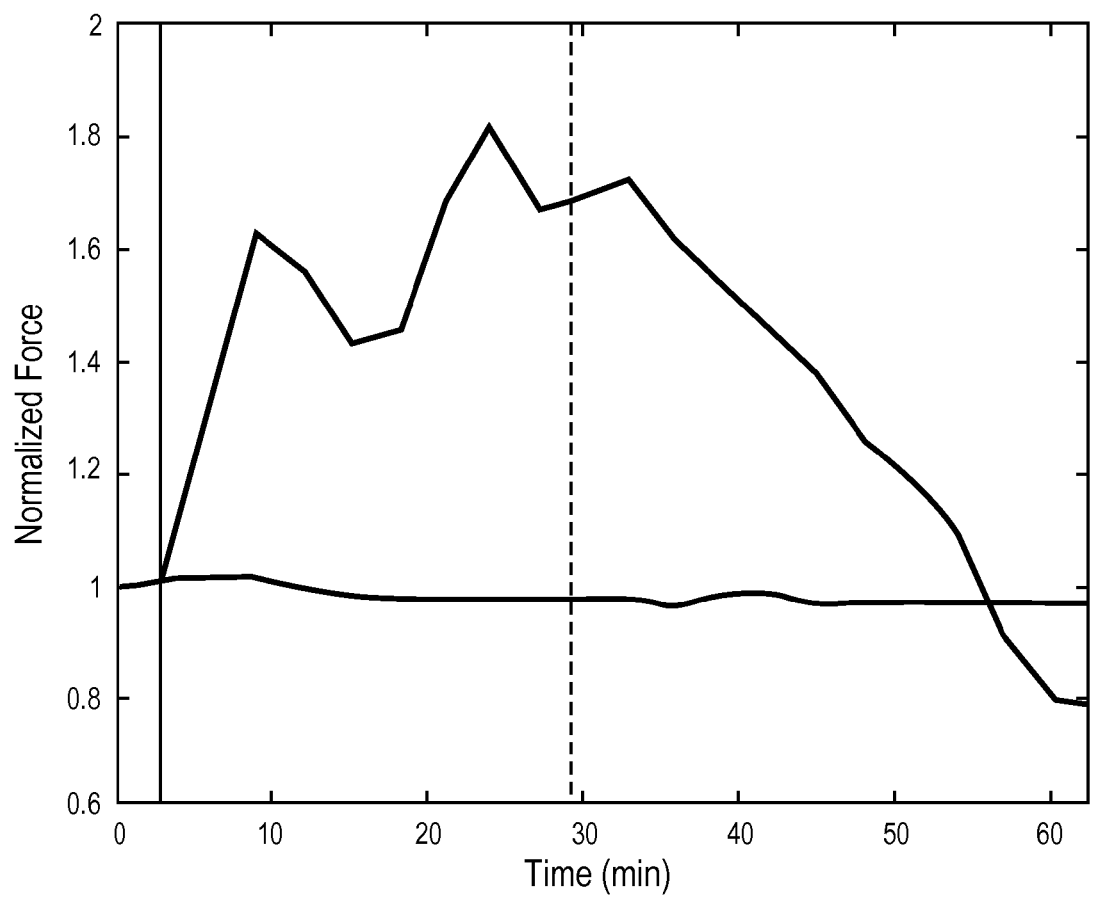
FIG. 17 shows empirical data from a human volunteer.

FIG. 17 shows empirical data from a human volunteer from the first study. The ordinate axis shows the maximum leg-extension force produced (as measured at the ankle by a dynamometer) by stimulation of the quadriceps muscle, normalized by baseline measurements for each leg. The electrical current settings on the NMES device were held constant throughout the measurement period. Time is shown on the abscissa. The measurements at time t=0-6 min were taken as baseline readings. At time t=6 min (solid vertical line), a waterproof bag containing ice cubes was used to cool superficial tissues on the experimental leg (upper data trace) in the location between the stimulation electrodes, while a room temperature bag was placed on the control leg (lower data trace). Both ice and room temperature bags were removed at time t=29 min (dotted vertical line). As shown, the improved efficiency of electrical current transfer to the quadriceps muscles (as evidenced by force of leg extension) is still evident more than 20 min following removal of the thermal stimulus. In addition to showing increased muscle stimulation (and increased contraction) FIG. 17 supports the functionality of cooling applied to superficial tissues intermittently during NMES or only prior to NMES.

Figure 18:
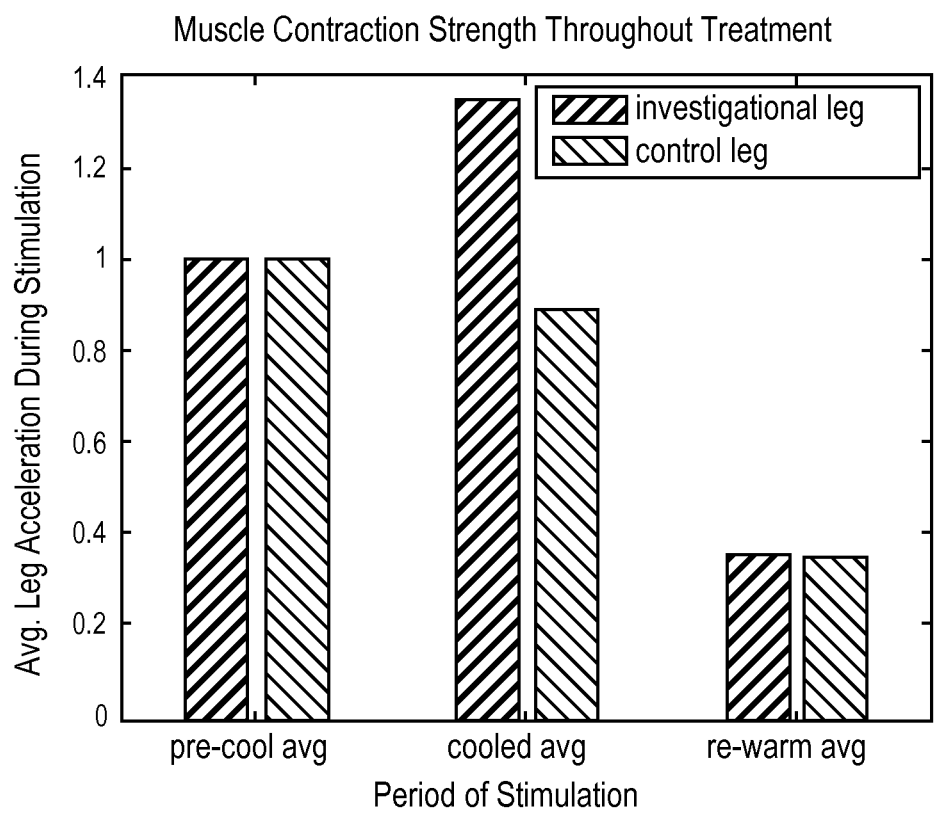
FIG. 18 shows empirical muscle stimulation data from a critically ill patient.

FIG. 18 shows empirical muscle stimulation data from a critically ill patient, which is part of the preliminary results from the second study. During stimulation, accelerometers placed on the patient's legs measured movement during stimulation of the quadriceps muscles. The amount of movement recorded is an adequate proxy for the degree to which a given amount of energy produces muscle contraction. After a series of baseline measurements acquired with both legs at body temperature were made (the set of columns on the far left), a temperature gradient was induced superficially on one leg with an ice bag while the other leg remained the body-temperature control. As shown by the center set of columns, muscle contraction strength improved during time periods when thermal stimuli were applied to the investigational leg but declined in the control leg. The decline in the control leg was likely due to fatigue. Relative to the control leg, muscle contraction was improved by 46%. Following the period of cooling, additional measurements were taken while the investigational leg was in the process of re-warming. As shown in the set of columns on the far right, contraction strength in both legs is once again similar, and dramatically less than at baseline. The decrease is again likely due to fatigue. The same energy was applied to both legs of the patient during pre-cooling, tissue cooling, and post-cool re-warming periods.

The disclosure herein generally describes muscle stimulation with an applied energy guidance field. In the embodiments herein the energy guidance field alters the electrical impedance in surface tissues and tissue proximate thereto. While one mechanism to generate the energy the guidance field is cooling the skin, other mechanisms may be used. For example, any of the following can theoretically be used, alone or in combination with other mechanisms, to generate the energy guidance field: 1) pulses or static electromagnetic fields, or magnet-based approaches in general; 2) applying a chemical agent topically or injecting a chemical agent to change conductive properties of local superficial tissues; 3) selective regional vasodilation (i.e., controlling how much blood vessels are constricted); 4) multiple energy source interference patterns to set up pathways of optimal transmission; and 5) injection of a temporary solution or material at depth to reduce the impedance of deep tissue.

The devices and methods described herein can be configured to be used on tissue surfaces inside the body as opposed to skin surfaces. In one example embodiment, surface electrodes are configured to stimulate the heart with trans-esophageal access. By applying a surface cooling device to the esophagus in a location between active stimulation electrodes, the efficiency of energy transfer to the heart may be improved. In one implementation of this embodiment, the cooling element is a compact pad with a hollow lumen, with a chilled fluid circulating through the lumen by way of small-sized inflow and outflow tubes. A variation of this embodiment with a slightly different configuration can be used in the application of diaphragmatic stimulation.

The methods described herein can be utilized effectively with any of the embodiments or variations of the devices and systems described above, as well as with other embodiments and variations not described explicitly in this document. The features of any of the systems or system components described in any of the embodiments herein can be used in any other suitable embodiment of a system or system component.

Various aspects of the invention described herein may be applied to any of the particular applications set forth below or for any other types of electrical stimulation and sensing systems or methods. The invention may be applied as a standalone system or method, or as part of an integrated medical treatment system. It shall be understood that different aspects of the invention can be appreciated individually, collectively, or in combination with each other.

The NMES system may be applied to any anatomical region of a subject, which may include a quadriceps region, or any other leg region. The NMES system may also be applicable to other anatomical regions as well. For example, the NMES system may target muscle tissue provided in the calves. In another example, the NMES system may target muscle tissue in the upper or lower arms. The NMES system may also target muscle tissue in the torso of a subject. For example, the system may provide stimulation to a subject's waist, or may provide stimulation to the subject's upper torso, and may use anatomical features such as armpits as a guide. The NMES system may target any other muscle tissue in a subject's body.

Any of the devices, systems, and methods described herein may incorporate suitable aspects, features, or steps used in other NMES applications. For example, the disclosure of U.S. patent application Ser. No. 12/497,230 filed Jul. 2, 2009 is hereby incorporated by reference in its entirety.

It should be understood from the foregoing that, while particular implementations have been illustrated and described, various modifications can be made thereto and are contemplated herein. It is also not intended that the disclosure be limited by the specific examples provided within the specification. Furthermore, it shall be understood that all aspects of the disclosure are not limited to the specific depictions, configurations or relative proportions set forth herein which depend upon a variety of conditions and variables. Various modifications in form and detail of the embodiments of the disclosure will be apparent to a person skilled in the art. It is therefore contemplated that the disclosure shall also cover any such modifications, variations and equivalents.

What is claimed is:

1. A muscle stimulation system, comprising:
a stimulation pad comprising a plurality of electrodes, wherein the stimulation pad is adapted to be positioned on the patient such that the electrodes are in position to provide stimulating energy to muscle tissue;
a cooling element adapted to be positioned on the patient between the plurality of electrodes and at a location that is different than the location on which the electrodes are positioned, and wherein the cooling element is configured to cool one or more superficial tissues to increase the impedance of the one or more superficial tissues, wherein the cooling increases the impedance of the one or more superficial tissue and drives a greater percentage of the stimulating energy deeper into the muscle tissue; and
a stimulation control unit in communication with the plurality of electrodes and configured to deliver the stimulating energy to the electrodes to stimulate the contraction of muscle tissue.

2. The system of claim 1 wherein the cooling element is configured to substantially avoid cooling of superficial tissue where the electrodes are positioned.

3. The system of claim 1 wherein the cooling element is adapted to substantially eliminate superficial current paths.

4. The system of claim 1 wherein the stimulation pad comprises the cooling element.

5. The system of claim 1 wherein the cooling element has a width and the plurality of electrodes span a width, and the width of the cooling element is greater than the width of the plurality of electrodes.

6. The system of claim 5 wherein the width of the cooling element is configured to substantially prevent superficial arcing around the cooling element.

7. The system of claim 1 further comprising a cooling element control unit which is adapted to control the operation of the cooling element.

8. The system of claim 7 wherein the cooling element control unit in is fluid communication with the cooling element and is configured to control the flow of a fluid through the cooling element.

9. The system of claim 8 wherein the cooling element control unit comprises a pump configured to pump the fluid through the cooling element.

10. The system of claim 7 wherein the cooling element comprises an internal lumen in fluid communication with the cooling element control unit.

11. The system of claim 7 wherein the cooling element control unit is configured to control a thermoelectric element.

12. A muscle stimulation system, comprising:
a plurality of stimulation electrodes adapted to be positioned on a subject;
a cooling element in communication with a cooling element control unit, wherein the cooling element control unit is configured to control the cooling element to decrease the temperature of one or more superficial tissues, wherein the decrease in temperature increases the impedance of the one or more superficial tissue and drives a greater percentage of stimulating energy deeper into the muscle tissue, and wherein the cooling element is configured to be positioned on the subject at a location where the plurality of stimulation electrodes are not positioned; and
a stimulation control unit in communication with the plurality of stimulating electrodes.

13. The system of claim 12 wherein the cooling element control unit is configured to control the temperature of the cooling element.

14. The system of claim 13 wherein the cooling element control unit is configured to maintain the cooling element at a substantially constant temperature.

15. The system of claim 13 wherein the cooling element control unit is configured to decrease the temperature of the cooling element after it has been activated.

16. The system of claim 12 wherein the cooling element control unit is configured to activate the cooling element.

17. The system of claim 16 wherein the cooling element control unit is configured to deactivate the cooling element while the stimulation control unit is delivering electrical stimulation to the plurality of electrodes.

18. The system of claim 16 wherein the cooling element control unit is configured to intermittently activate the cooling element.

19. The system of claim 12 wherein the cooling element is sized and shaped to be disposed between the plurality of stimulation electrodes.

20. The system of claim 19 wherein the cooling element is sized and shaped to be disposed at least partially surrounding the plurality of electrodes.

21. The system of claim 12 wherein the plurality of electrodes are integrated into a simulation pad.

22. The system of claim 12 wherein the cooling element is integrated into the stimulation pad.

23. The system of claim 12 wherein the cooling element has an internal lumen therein in fluid communication with the cooling element control unit, and wherein the cooling element control unit comprises a pump to pump fluid through the cooling element.

24. The system of claim 12 wherein the control element is a thermoelectric device, and wherein the cooling element control unit is adapted to control the thermoelectric device.

25. The system of claim 1 wherein the stimulation control unit is configured to deliver the stimulating energy at less than 100 kHz to stimulate the contraction of muscle tissue.

26. A muscle stimulation system, comprising:
a plurality of stimulation electrodes adapted to be positioned relative to a subject such that the plurality of electrodes are in a position to provide stimulating energy to muscle tissue;
a cooling element configured to cool one or more superficial tissues, wherein the cooling element is disposed such that it does not completely overlap the plurality of stimulation electrodes; and
a stimulation control unit in communication with the plurality of electrodes and configured to deliver the stimulating energy to the electrodes to stimulate the contraction of muscle tissue.

27. The system of claim 26 wherein the cooling element is disposed relative to the plurality of stimulation electrodes such that it substantially avoids cooling of superficial tissue where the electrodes are positioned.

28. The system of claim 26 further comprising a stimulation pad that comprises the plurality of electrodes.

29. The system of claim 28 wherein the stimulation pad is secured to the cooling element.

30. The system of claim 28 wherein the cooling element has a width and the plurality of electrodes span a width, and the width of the cooling element is greater than the spanning width of the plurality of electrodes.

31. The system of claim 30 wherein the width of the cooling element is configured to substantially prevent superficial arcing around the cooling element.

32. The system of claim 26 further comprising a cooling element control unit that is adapted to control the operation of the cooling element.

33. The system of claim 32 wherein the cooling element control unit in is fluid communication with the cooling element and is configured to control the flow of a fluid through the cooling element.

34. The system of claim 33 wherein the cooling element control unit comprises a pump configured to pump the fluid through the cooling element.

35. The system of claim 32 wherein the cooling element comprises an internal lumen in fluid communication with the cooling element control unit.

36. A muscle stimulation system, comprising:
a stimulation pad comprising a plurality of stimulation electrodes, wherein the stimulation pad is adapted to be disposed relative to the patient such that the electrodes are in position to provide stimulating energy to muscle tissue;
a cooling element configured to cool one or more superficial tissues, wherein the cooling element is disposed between the plurality of stimulation electrodes such that it cools superficial tissue between the plurality of electrodes, wherein the cooling increases the impedance of the one or more superficial tissue and drives a greater percentage of the stimulating energy deeper into the muscle tissue; and
a stimulation control unit in communication with the plurality of stimulation electrodes and configured to deliver the stimulating energy to the plurality of stimulation electrodes to stimulate the contraction of muscle tissue.

37. The system of claim 36 wherein the stimulation pad is secured to the cooling element.

38. The system of claim 36 wherein the cooling element has a width and the plurality of electrodes span a width, and the width of the cooling element is greater than the spanning width of the plurality of stimulation electrodes.

39. The system of claim 36 wherein the cooling element is disposed such that it does not completely overlap the plurality of stimulation electrodes.

40. The system of claim 36 wherein the cooling element is disposed relative to the plurality of stimulation electrodes such that it substantially avoids cooling of superficial tissue where the plurality of stimulation electrodes are positioned.

41. The system of claim 36 further comprising a cooling element control unit that is adapted to control the operation of the cooling element.

42. The system of claim 26 wherein the cooling element is adapted to substantially eliminate superficial current paths.

43. The system of claim 28 wherein the stimulation pad comprises the cooling element.

44. The system of claim 32 wherein the cooling element control unit is configured to control a thermoelectric element.

45. The system of claim 26 wherein the stimulation control unit is configured to deliver the stimulating energy at less than 100 kHz to stimulate the contraction of muscle tissue.

46. The system of claim 26 wherein the cooling element is disposed in a centralized region between the plurality of electrodes.

47. The system of claim 26 wherein the cooling element is disposed such that it overlaps at most 50% of the area encompassed by the plurality of electrodes.

48. The system of claim 26 wherein the cooling element is disposed such that there is no overlap of the cooling element and the plurality of electrodes.

49. The system of claim 26 wherein the cooling element is disposed relative the plurality of electrodes such that it cools superficial tissue between the electrodes more than superficial tissue near the electrodes.

\* \* \* \* \*